(12) United States Patent
Richardson

(10) Patent No.: US 6,649,345 B2
(45) Date of Patent: Nov. 18, 2003

(54) PHENYLALANINE HYDROXYLASE GENE VARIANTS, AND AMINO ACID AND PTERIN HOMEOSTASIS, IN THE DEFINITION, DETECTION, TREATMENT AND PREVENTION OF PSYCHOTIC, MOOD AND PERSONALITY DISORDERS

(75) Inventor: Mary Ann Richardson, New York, NY (US)

(73) Assignee: New York State Office of Mental Health, Albany, NY (US)

( * ) Notice: Subject to any disclaimer, the term of this patent is extended or adjusted under 35 U.S.C. 154(b) by 170 days.

(21) Appl. No.: 09/734,188

(22) Filed: Dec. 12, 2000

(65) Prior Publication Data

US 2002/0106645 A1 Aug. 8, 2002

Related U.S. Application Data

(62) Division of application No. 09/253,025, filed on Feb. 19, 1999, now Pat. No. 6,200,758.

(51) Int. Cl.$^7$ .......................... C12Q 1/68; C07H 19/00; C07H 19/048; C07H 5/06
(52) U.S. Cl. .............................. 435/6; 435/810; 536/27; 536/28; 536/29; 935/77; 935/78
(58) Field of Search ....................... 435/6, 810; 536/27, 536/28, 29; 935/77, 78

(56) References Cited

U.S. PATENT DOCUMENTS

| | | | |
|---|---|---|---|
| 4,965,190 A | | 10/1990 | Woo et al. |
| 5,393,784 A | | 2/1995 | Richardson |
| 5,670,539 A | | 9/1997 | Richardson |
| 5,919,823 A | | 7/1999 | Richardson |
| 6,025,193 A | | 2/2000 | Weiss |
| 6,026,322 A | * | 2/2000 | Korenman .................. 600/547 |
| 6,034,091 A | | 3/2000 | Dante |
| 6,117,890 A | * | 9/2000 | Bymaster .................... 514/342 |

OTHER PUBLICATIONS

Abola EE et al., "Protein data bank archives of three–dimensional macromolecular structures" *Methods Enzymol* 1997; 277:556–571.

Aebischer P et al., "Long–term cross–species brain transplantation of a polymer–ncapsulated dopamine–secreting cell line" *Experimental Neurology* 1991; 111: 269–275.

Andreou ER and Prokipcak D, "Analysis of human CYP7A1 mRNA decay in Hep–G2 cells by reverst transcription–polymerase chain reaction" *Arch Biochem Biophys* 1998; 357: 137–146.

Berry HK et al., "Reduction of cerebrospinal fluid phenylalanine after oral administration of Valine, Isoleucine, and Leucine" *Pediatr Res* 1982; 16: 751–755.

Berry HK et al., "Preliminary support for the oral administration of Valine, Isoleucine and Leucine for phenylketonuria" *Dev Med Child Neurol* 1985; 27: 33–39.

Berry HK et al., "Valine, Isoleucine, and Leucine" *Amer J of Diseases of Children* 1990; 144: 539–543.

Bjerkenstedt L et al., "Plasma amino acids in relation to cerebrospinal fluid monoamine metabolites in schizophrenic patients and healthy controls" *Br J Psychiatry* 1985; 147: 276–282.

Bjorgo E et al., "Partial characterization and three–dimensional–structural localization of eight mutations in exon 7 of the human phenylalanine hydroxylase gene associated with phenylketonuria" *Eur J Biochem* 1998; 257: 1–10.

Blumenthal MD, "Mental illness in parents of phenylketonuric children" *J Psychiatr Res* 1967; 5: 59–74.

Boulton AA et al., "Phenylethylamine int he CNS: effects of monoamine oxidase inhibiting drugs, deuterium substitution and lesions and its role in the neuromodulation of catecholaminergic neurotransmission" *J Neural Transmission Suppl* 1990; 29: 119–129.

Burcin MM et al., "Adenovirus–mediated regulable target gene expression in vivo" *Proc Nat Acad Sci USA* 1999; 96: 355–360.

Caballero B and Wurtman RJ, "Control of Plasma phenylalanine levels" Ch. 1, In: Wurtman RJ and Ritter–Walker E, eds. *Dietary Phenylalanine and Brain Function*. Boston: Birkhauser, 1988; 9–23.

Cloninger CR et al., "Genome–wide search for schizophrenia susceptibility loci: The NIMH genetics initiative and millennium consortium" *Am J Med Genet* 1998; 81: 275–281.

Cole SP et al., "Human monoclonal antibodies" *Mol Cell Biochem* 1984; 62: 109–120.

Daniel PM et al., "Amino acid precursors of monoamine neurotransmitters and some factors influencing their supply to the brain" *Psychol Med* 1976; 6: 277–286.

Dawson E et al., "Genetic association between alleles of pancreatic phospholipase A2 gene and bipolar affective disorder" *Psychiatric Genetics* 1995; 5: 177–180.

Desviat LR et al., "Molecular basis of non–PKU hyperphenylalaninaemia in Spain: Prevalence of A403V, a mutation with high residual activity" *J inherit Metab Dis* 1996; 19: 227–230.

(List continued on next page.)

Primary Examiner—Gary Benzion
Assistant Examiner—Arun Kr. Chakrabarti
(74) *Attorney, Agent, or Firm*—Sughrue Mion, PLLC

(57) ABSTRACT

The present invention describes sequence variants in the phenylalanine hydroxylase gene, and biochemical measures of amino acid and pterin homeostasis, which are associated with Psychotic, Mood and Personality Disorders. Methods for the definition of etiological/pathophysiological subtypes of the disorders and for the detection of disorder susceptibility are provided. Treatment and prophylactic strategies targeted at the elaborated psychopathology are also disclosed.

4 Claims, No Drawings

OTHER PUBLICATIONS

Dickson PW et al., "Delineation of the Catalytic core of phenylalanine hydroxylase and identification of glutamate 286 as a critical residue for pterin function" *J Biol Chem* 1994; 269: 20369–20375.

DiLella AG et al., "Molecular structure and polymorphic map of the human phenylalanine hydroxylase gene" *Biochemistry* 1986; 25: 743–749.

Dourish CT, "Behavioural effects of acute and chronic B–phenylethylamine administration in the rat: Evidence of the involvement of 5–hydroxytryptamine" *Neuropharmacology* 1981; 20: 1067–1072.

Dworniczak B et al., "Aberrant splicing of phenylalanine hydroxylase mRNA: The major cause for phenylketonuria in parts of Southern Europe" *Genomics* 1991; 11: 242–6.

Eisenberg D et al., "The hydrophobic moment detects periodicity in protein hydrophobicity" *Proc Natl Acad Sci USA* 1984; 81: 140–144.

Faraone SV et al., "Genome scan of European–American schizophrenia pedigrees: Results of the NIMH genetics initiative and millennium consortium" *Am J Med Genet* 1998; 81: 290–295.

Fischer E et al., "Urinary elimination of phenethylamine" *Biol Psychiatry* 1972; 5: 139–147.

Folstein MF and Folstein SE, "Mini–Mental State" *J Psychiat Res* 1975; 12: 189–198.

Fukushima T and Nixon JC, "Analysis of reduced forms of biopterin in biological tissues and fluids" *Analytical Biochemistry* 1980; 102: 176–188.

Fusetti F et al., "Structure of tetrameric human phenylalanine hydroxylase and its implications for phenylketonuria" *J Biol Chem* 1998; 273: 16962–16967.

Gardos G et al., "The acute effects of a loading dose of phenylalanine in unipolar depressed patients with and without tardive dyskinesia" *Neuropsychopharmacology* 1992; 6: 241–247.

Garnier J, "Analysis of the accuracy and implications of simple methods for predicting the secondary structure of globular proteins" *J Mol Biol* 1978; 120: 97–120.

Ghosh S and Collins FS, "The geneticist's approach to complex disease" *Annu Rev Med* 1996; 47: 333–353.

Gill SC and von Hippel PH, "Calculation of protein extinction coefficients from amino acid sequence data" *Anal Biochem* 1989; 182: 319–326.

Guex N and Peitsh NC, "Swiss–Model and the Swiss–Pdb viewer: An environment for comparative protein modeling" *Electrophoresis* 1997; 18: 2714–2723.

Guldberg P et al., "Molecular analysis of phenylketonuria in Denmark: 99% fo the mutations detected by denaturing gradient gel electrophoresis" *Genomics* 1993; 17: 141–6.

Guldberg P and Guttler F, "A simple method for identification of point mutations using denaturing gradient gel electrophoresis" *Nucleic Acids Res* 1993; 21: 2261–2.

Guldberg P et al., "Mutational spectrum of phenylalanine hydroxylase deficiency in Sicily: implications for diagnosis of hyperphenylalaninemia in southern Europe" *Human Molecular Genetics* 1993; 2: 1703–1707.

Guldberg P et al., "Phenylalanine hydroxylase gene mutations in the United States: Report from the maternal PKU collaborative study" *Am J Hum Genet* 1996; 59: 84–94.

Guldberg P et al., "A European multicenter study of phenylalanine gydroxylase deficiency: Classification of 105 mutations and a general system for genotype–based prediction of metabolic phenotype" *Am J Hum Genet* 1998; 63: 71–79.

Guttler F et al., "Combined tetrahydrobiopterin–phenylalanine loading test in the detection of partially defective biopterin synthesis" *Eur J Pediatr* 1984; 142: 126–129.

Hamilton M, "A Rating Scale for Depression" *J Neurol Neurosurg Psychiat* 1960; 23: 56–62.

Hariharan M et al., "Systematic approach to the development of plasma amino acid analysis by high–performance liquid chromatography with ultraviolet detection with pre-column derivatization using phenl isothiocyanate" *J Chromatogr* 1993; 621: 15–22.

Hufton SE et al., "Structure and function of the aromatic amino acid hydroxylases" *Biochem J* 1995; 311: 353–366.

Hyland K et al., "Oral phenylalanine loading in dopa–responsive dystonia: A possible diagnostic test" *Neurology* 1997; 48: 1290–1297.

Jennings IG et al., "Localization of cofactor binding sites with monoclonal anti–idiotype antibodies: Phenylalanine hydroxylase" *Proc Natl Acad Sci USA* 1991; 88: 5734–5738.

Jeste DV et al., "Cross–Cultural study of a biochemical abnormality in Paranoid Schizophrenia" *Psychiatry Res* 1981; 5:341–352.

Kay AD et al., "Cerebrospinal fluid biopterin is decreased in Alzheimer's Disease" *Arch Neurol* 1986; 43: 996–999.

Kuznetsova LI, "Frequency and phenotypic manifestations of schizophrenia in the patients with phenylketonuria" *Sov Genet* 1974; 8: 554–555.

Larson CA and Nyman GE, "Phenylketonuria: Mental illness in heterozygotes" *Psychiatr Clin* 1968; 1: 367–374.

Lehnert H and Wurtman RJ, "Amino acid control of neurotransmitter synthesis and release: Physiological and clinical implications" *Psychotherapy & Psychosomatics* 1993; 60: 18–32.

Levine RA, "Tetrahydrobiopterin and biogenic amine metabolism in neuropsychiatry, immunology, and aging" *Annals of the NY Academy of Sciences* 1988; 521: 129–139.

Lidsky AS et al., "Regional mapping of the phenylalanine hydroxylase gene and the phenylketonuria locus in the human genome" *Proc Natl Acad Sci USA* 1985; 82: 6221–6225.

Lunte CE and Kissinger PT, "Determination of pterins in biological samples by liquid chromatography/electrochemistry with a dual–electrode detector" *Analytical Chemistry* 1983; 55: 1458–1462.

Maher T, "Effects of phenylalanine on the synthesis, release, and function of catecholaminergic systems" Ch.6, In: Richardson MA, eds. *Amino Acids in Psychiatric Disease*. Washington, D.C.: American Psychiatric Press, Inc., 1990; 131–142.

Merrick WC and Sonenberg N, "Assays for eukaryotic translation factors that bind mRNA" *Methods* 1997; 11: 333–342.

Nurnberger JI, Jr. et al., "Genomic survey of bipolar illnes in the NIMH genetics initiative pedigrees: A preliminary report" *Am J Med Genet* 1997; 74: 227–237.

O'Malley MP et al., "Linkage analysis between schizophrenia and Darier's disease region on 12q" *Psychiatr Genet* 1996; 6: 187–190.

O'Reilly R et al., "Plasma phenylethylamine in schizophrenic patients" *Biol Psychiatry* 1991; 30: 145–150.

Orita M et al., "Detection of polymorphisms of human DNA by gel electrophoresis as single–stranded conformation polymorphisms" *Proc Natl Acad Sci USA* 1989; 86: 2766–2760.

Overall JE and Gorham DR, "The Brief Psychiatric Rating Scale" 1962; 10: 799–812.

Pardridge WM and Choi TB, "Neutral amino acid transport at the human blood–brain barrie" *Federation Proceedings* 1986; 45: 2073–2078.

Perry TL and Chapple JA, "The incidence of mental illness in the relatives of individuals suffering from phenylketonuria or mongolism" *J psychiatr Res* 1966; 4: 51–57.

Picciotto MR and Wickman K, "Using knockout and transgenic mice to study neurophysiology and behavior" *Physiol Rev* 1998; 78: 1131–63.

Pietz J et al., Psychiatric disorders in adult patients with early–treated phenylketonuria: *Pediatrics* 1997; 99: 345–350.

Poisner AM, "Serum phenylalanine in schizophrenia: Biochemical genetic aspects" *J Nerv Ment Dis* 1960; 131: 74–76.

Potkin SG et al., "Psychostimulants and dopamine agonists int eh study of adult hyperkinesis, schizophrenia, and affective disorders" *Psychopharmacol Bull* 1980; 16:52–54.

Potkin SG et al., "Plasma phenylalanine, tyrosine, and tryptophan in schizophrenia" *Arch Gen Psychiatry* 1983; 40: 749–752.

Pratt RTC et al., "Phenylalanine tolerance in endogenous depression" *Brit J Psychiat* 1963; 109: 624–628.

Rao ML et al., "Serum amino acids, central monoamines, and hormones in drug–naive, drug–free, and neuroleptic–treated schizophrenic patients and healthy subjects" *Psychiatry Res* 1990; 34: 243–257.

Rein T et al., "Identifying 5–methylcytosine and related modifications in DNA genomes" *Nucleic Acids Res* 1998; 26: 2255–2264.

Richardson MA et al., "The prevalence of tardive dyskinesia in a mentally retarded population" *Psychopharmacol Bull* 1986; 22: 243–249.

Richardson MA et al., "The plasma phenylalanine/large neutral amino acid ratio: A risk factor for tardive dyskinesia" *Psychopharmacol Bull* 1989; 25: 47–51.

Richardson MA et al., "Plasma phenylalanine: A measure of tardive dyskinesia vulnerability in schizophrenic males" Ch.7, In: Richardson MA, eds. *Amino Acids in Psychiatric Disease*. Washington, D.C.: American Psychiatric Press, Inc., 1990: 143–160.

Richardson MA et al., "Phenylalanine to serotonin to tardive dyskinesia: A new model" *Proceedings of the 2nd International Symposium on Serotonin, from cell Biology to Pharmacology and therapeutics*, Houston, Texas 1992; Sep. 15–18.

Richardson MA et al., "Comment on 'The ratio of plasma phenylalanine to other large neutral amino acids is not a risk factor for tardive dyskinesia'" *J Psychopharm* 1993; 7: 219–220.

Richardson MA et al., "TD and phenylalanine metabolism: Sex and age issues" *Schizophrenia Research* 1996; 18: 149.

Richardson MA et al., "A dietary intervention decreases tardive dyskinesia symptoms" *Am Psychiatr Assoc, 149th Annual Meeting*, NY, NY 1996; O: 194.

Richardson MA et al., "TD symptom decreases with regulation of plasma large neutral amino acids" *Abstracts, 16th International Congress of Nutrition*, Montreal, Canada 1997; O: 42.

Richardson MA et al., "TD symptom decreases with regulation of plasma large neutral amino acids" *Schizophrenia Research* 1997; 24: 272.

Richardson MA et al., "Tardive dyskinesia and phenylalanine metabolism: risk–factor studies" Ch.13, In: Yassa R et al., eds. *Neuroleptic–Induced Movement Disorders*. Cambridge: Cambridge University Press, 1997: 161–174.

Richardson MA et al., "Branched chain amino acids decrease TD symptoms" *Psychopharmacology*, IN PRESS.

Richardson MA et al., "Phenylalanine kinetics are associated with TD in men but not in women" *Psychopharmacology*, IN PRESS.

Scriver CR and Rosenberg LE, "Phenylalanine" Ch. 15, In: Schaffer AL, eds. *Amino Acid Metabolism and its Disorders*. Philadelphia, 1973; 290–337.

Scriver CR, Whatever happened to PKU? *Clin Biochem* 1995; 28: 137–144.

Shaw SH et al., "A genome–wide search for schizophrenia susceptibility genes" *Am J Med Genet* 1998; 81: 364–376.

Sloviter RS et al., "Serotonergic properties of B–phenethylamine in rats" *Neuropharmacology* 1980; 19: 1071–1074.

Snyder SH, "Amphetamine psychosis: A 'Model' schizophrenia mediated by catecholamines" *Am J Psychiatry* 1973; 130: 61–67.

Sobell JL et al., "Novel association approach for determining the genetic predisposition to schizophrenia: Case–control resource and testing of a candidate gene" *Am J Med Genet* 1993; 48: 28–35.

Szymanski HV et al., "Plasma phenylethylamine and phenylalanine in chronic schizophrenic patients" *Biol Psychiatry* 1987; 22: 194–198.

Tang MX et al., "The APOE–e4 allele and the risk of alzheimer disease among African Americans, whites, and hispanics" *JAMA* 1998; 279: 751–755.

Targum SD et al., "Screening for PKU heterozygosity in bipolar affectively ill patients" *Biol Psych* 1979; 14: 651–655.

Thompson JH, "Relatives of phenylketonuric patients" *J Ment Defic Res* 1957; 1: 67–78.

Waters PJ et al., "In vitro expression analysis of mutations in phenylalanine hydroxylase: Linking genotype to phenotypw and structure to function" *Hum Mutat* 1998; 11: 4–17.

Wyatt RJ et al., "Phenylethylmine (PEA) and chronic schizophrenia", *Catecholamines: Basic and Clinical Frontiers*. In: Usdin K, et al., eds. New York: Raven Press, 1979; 1833–1835.

Ye X et al., "Regulated delivery of therapeutic proteins after in vivo somatic cell gene transfer" *Science* 1999; 283: 88–94.

Yoshimoto S et al., "Urinary trace amine excretion and platelet monoamine oxidase activity in schizophrenia" *Psychiatry Res* 1987; 21: 229–236.

Zekanowski C et al., "Molecular basis of mild hyperphenylalaninaemia in Poland" *J Med Genet* 1997; 34: 1035–1036.

1998 World Congress on psychiatric Genetics, *Am J Med Genet* 1998; 81: 451–556.

Mutation ID 936854085 (N426N mutation), Phenylalanine Hydroxylase Locus Knowledgebase (PAHdb; http://data.mch.mcgill.ca/cgl–bln/pahdb_new/q_mut.cgl), listed as published on Sep. 9, 1999.

Mutation ID 929464820 (L321L mutation), Phenylalanine Hydroxylase Locus Knowledgebase (PAHdb; http://data.mch.mcgill.ca/cgl–bln/pahdb_new/q_mut.cgl), listed as published on Jun. 15, 1999.

Kwok et al. "Nucleotide Sequence of a Full–length Complementary DNA Clone and Amino Acid Sequence of Human Phenylalanine Hydroxylase", Biochemistry, vol. 24, pp. 556–561.

The American Socieity of Human Genetics, "The American Journal of Human Genetics," Supplement to vol. 63, Program Nr: 2011 (1998).

Kenneth S. Kendler, et al. "Schizotypal Symptoms and Signs in the Roscommon Family Study–Their Factor Structure and Familial Relationship with Psychotic and Affective Disorder" Arch Gen. Psychiatry 1995, vol. 52, pp. 296–303.

George Winokur, M.D., et al. "The Iowa 500: Affective Disorder in Relatives of manic and Depressed Patients" American Journal of Psychiatry vol. 139:Feb. 2, 1982, pp. 209–212.

Elliot S. Gershon, M.D., et al. "A Controlled Family Study of Chronic Psychoses—Schizophrenia and Schizoaffective Disorder" Arch Gen. Psychiatry 1988; vol. 45: pp. 328–336.

Jeremy M. Silverman Ph.D., et al. "Schizophrenia–Related and Affective Personality disorder Traits in Relatives of Probands With Schizophrenia and Personality Disorders" American Journal of Psychiatry vol. 150:Mar. 3, 1993 pp. 435–442.

Wade H. Berrettini, "Genetics of Pshchiatric Disease" Annu. Rev. Med. 2000, vol. 51: pp. 465–479.

Kenneth S. Kendler, et al. "The Roscommon Family Study II. The Risk of Nonschizophrenic Nonaffective Psychoses in Relatives" Arch Gen. Psychiatry, 1993; vol. 50: pp. 645–652.

Sarah Henn et al., Affective illeness and schizophrenia in families with multiple schizophrenic members: independent illnesses or variant genes)? European Neuropsychopharmacology Supplement 1995, pp. 31–36.

Kenneth S. Kendler, et al. "The risk of psychiatric disorders in relatives of schizophrenic and control probands: a comparision of three independent studies" Psychological Medicine, 1997, vol. 27, pp. 411–419.

Michael J. Lyons, et al. "Comparision of Schizotypal Relatives of Schizophrenic Versus Affective Probands" American Journal of Mdical Genetics (Neuropsychiatric Genetics) vol. 54: pp. 279–285, 1994.

Elliott S. Gershom, et al. "A Family Study of Schizoaffective, Bipolar I, Bipolar II, Unipolar, and Norm Control Probands" Arch Gen. Psychiatry, vol. 39, Oct. 1982, pp. 1157–1167.

Shashjit Lal Varma, et al., "Psychiatric Morbidity in the First–Degree Relatives of schizophrenic Patients." American Journal of Medical Genetics (Neuropsychiatric Genetics) vol. 74: pp. 7–11. 1997.

* cited by examiner

SEQUENCE LISTING

<160> NUMBER OF SEQ ID NOS: 62

<210> SEQ ID NO 1
<211> LENGTH: 60
<212> TYPE: DNA
<213> ORGANISM: Homo sapiens

<400> SEQUENCE: 1
cgcccgccgc gccccgcgcc cgtcccgccg ccccccgcccg ttaaaacctt cagccccacg        60

<210> SEQ ID NO 2
<211> LENGTH: 24
<212> TYPE: DNA
<213> ORGANISM: Homo sapiens

<400> SEQUENCE: 2
tggaggccca aattcccta actg        24

<210> SEQ ID NO 3
<211> LENGTH: 24
<212> TYPE: DNA
<213> ORGANISM: Homo sapiens

<400> SEQUENCE: 3
gaggtttaac aggaatgaat tgct        24

<210> SEQ ID NO 4
<211> LENGTH: 60
<212> TYPE: DNA
<213> ORGANISM: Homo sapiens

<400> SEQUENCE: 4
cgcccgccgc gccccgcgcc cgtcccgccg ccccccgcccg tcctgtgttc ttttcattgc        60

<210> SEQ ID NO 5
<211> LENGTH: 60
<212> TYPE: DNA
<213> ORGANISM: Homo sapiens

<400> SEQUENCE: 5
cgcccgccgc gccccgcgcc cgtcccgccg ccccccgcccg gcctgcgtta gttcctgtga        60

<210> SEQ ID NO 6
<211> LENGTH: 20
<212> TYPE: DNA
<213> ORGANISM: Homo sapiens

-continued

```
<400> SEQUENCE: 6
cttatgttgc aaaattcctc                                              20

<210> SEQ ID NO 7
<211> LENGTH: 25
<212> TYPE: DNA
<213> ORGANISM: Homo sapiens

<400> SEQUENCE: 7
atgttctgcc aatctgtact cagga                                        25

<210> SEQ ID NO 8
<211> LENGTH: 60
<212> TYPE: DNA
<213> ORGANISM: Homo sapiens

<400> SEQUENCE: 8
cgcccgccgc gccccgcgcc cgtcccgccg ccccgcccg caagacatag gccatggact    60

<210> SEQ ID NO 9
<211> LENGTH: 20
<212> TYPE: DNA
<213> ORGANISM: Homo sapiens

<400> SEQUENCE: 9
tcatggcttt agagccccca                                              20

<210> SEQ ID NO 10
<211> LENGTH: 60
<212> TYPE: DNA
<213> ORGANISM: Homo sapiens

<400> SEQUENCE: 10
cgcccgccgc gccccgcgcc cgtcccgccg ccccgcccg aggctagggg tgtgttttc    60

<210> SEQ ID NO 11
<211> LENGTH: 60
<212> TYPE: DNA
<213> ORGANISM: Homo sapiens

<400> SEQUENCE: 11
cgcccgccgc gccccgcgcc cgtcccgccg ccccgcccg ccgactccct ctgctaacct   60

<210> SEQ ID NO 12
<211> LENGTH: 20
<212> TYPE: DNA
<213> ORGANISM: Homo sapiens

<400> SEQUENCE: 12
caatcctccc ccaactttct                                              20

<210> SEQ ID NO 13
<211> LENGTH: 65
<212> TYPE: DNA
<213> ORGANISM: Homo sapiens

<400> SEQUENCE: 13
cgcccgccgc gccccgcgcc cgtcccgccg ccccgcccg ggtgatgagc ttttagtttt   60
ctttc                                                              65

<210> SEQ ID NO 14
<211> LENGTH: 20
```

```
<212> TYPE: DNA
<213> ORGANISM: Homo sapiens

<400> SEQUENCE: 14
agcaaatgaa cccaaacctc                                             20

<210> SEQ ID NO 15
<211> LENGTH: 60
<212> TYPE: DNA
<213> ORGANISM: Homo sapiens

<400> SEQUENCE: 15
cgcccgccgc gccccgcgcc cgtcccgccg ccccgcccg tggcttaaac ctcctcccct   60

<210> SEQ ID NO 16
<211> LENGTH: 20
<212> TYPE: DNA
<213> ORGANISM: Homo sapiens

<400> SEQUENCE: 16
ctgggctcaa ctcatttgag                                             20

<210> SEQ ID NO 17
<211> LENGTH: 20
<212> TYPE: DNA
<213> ORGANISM: Homo sapiens

<400> SEQUENCE: 17
atggccaagt actaggttgg                                             20

<210> SEQ ID NO 18
<211> LENGTH: 60
<212> TYPE: DNA
<213> ORGANISM: Homo sapiens

<400> SEQUENCE: 18
cgcccgccgc gccccgcgcc cgtcccgccg ccccgcccg gagggccata gactatagca   60

<210> SEQ ID NO 19
<211> LENGTH: 60
<212> TYPE: DNA
<213> ORGANISM: Homo sapiens

<400> SEQUENCE: 19
cgcccgccgc gccccgcgcc cgtcccgccg ccccgcccg ttaacgatca tagagtgtgc   60

<210> SEQ ID NO 20
<211> LENGTH: 24
<212> TYPE: DNA
<213> ORGANISM: Homo sapiens

<400> SEQUENCE: 20
ttaaatctat ccttggttcc tgtg                                        24

<210> SEQ ID NO 21
<211> LENGTH: 20
<212> TYPE: DNA
<213> ORGANISM: Homo sapiens

<400> SEQUENCE: 21
tgagagaagg ggcacaaatg                                             20

<210> SEQ ID NO 22
```

```
<211> LENGTH: 60
<212> TYPE: DNA
<213> ORGANISM: Homo sapiens

<400> SEQUENCE: 22
cgcccgccgc gccccgcgcc cgtcccgccg ccccgcccg gccaaccacc cacagatgag       60

<210> SEQ ID NO 23
<211> LENGTH: 20
<212> TYPE: DNA
<213> ORGANISM: Homo sapiens

<400> SEQUENCE: 23
atgccactga gaactctctt                                                  20

<210> SEQ ID NO 24
<211> LENGTH: 60
<212> TYPE: DNA
<213> ORGANISM: Homo sapiens

<400> SEQUENCE: 24
cgcccgccgc gccccgcgcc cgtcccgccg ccccgcccg gattactgag aaagtggcct       60

<210> SEQ ID NO 25
<211> LENGTH: 60
<212> TYPE: DNA
<213> ORGANISM: Homo sapiens

<400> SEQUENCE: 25
cgcccgccgc gccccgcgcc cgtcccgccg ccccgcccg gacacttgaa gagttttgc       60

<210> SEQ ID NO 26
<211> LENGTH: 20
<212> TYPE: DNA
<213> ORGANISM: Homo sapiens

<400> SEQUENCE: 26
ttttcggact ttttctgatg                                                  20

<210> SEQ ID NO 27
<211> LENGTH: 21
<212> TYPE: DNA
<213> ORGANISM: Homo sapiens

<400> SEQUENCE: 27
tacaatcatg cttgtcttgg a                                                21

<210> SEQ ID NO 28
<211> LENGTH: 21
<212> TYPE: DNA
<213> ORGANISM: Homo sapiens

<400> SEQUENCE: 28
gtactcagga tgttgccttc t                                                21

<210> SEQ ID NO 29
<211> LENGTH: 21
<212> TYPE: DNA
<213> ORGANISM: Homo sapiens

<400> SEQUENCE: 29
tcttcttttc ttcccagctt g                                                21
```

```
<210> SEQ ID NO 30
<211> LENGTH: 21
<212> TYPE: DNA
<213> ORGANISM: Homo sapiens

<400> SEQUENCE: 30
gatttgccaa ccagattctc a                                              21

<210> SEQ ID NO 31
<211> LENGTH: 21
<212> TYPE: DNA
<213> ORGANISM: Homo sapiens

<400> SEQUENCE: 31
acgtttctca gttcctgcag a                                              21

<210> SEQ ID NO 32
<211> LENGTH: 21
<212> TYPE: DNA
<213> ORGANISM: Homo sapiens

<400> SEQUENCE: 32
tccgacctgt agctggcctg c                                              21

<210> SEQ ID NO 33
<211> LENGTH: 21
<212> TYPE: DNA
<213> ORGANISM: Homo sapiens

<400> SEQUENCE: 33
ttgaaaagct tgccacagta a                                              21

<210> SEQ ID NO 34
<211> LENGTH: 21
<212> TYPE: DNA
<213> ORGANISM: Homo sapiens

<400> SEQUENCE: 34
tccagcccct ctattacgtg g                                              21

<210> SEQ ID NO 35
<211> LENGTH: 21
<212> TYPE: DNA
<213> ORGANISM: Homo sapiens

<400> SEQUENCE: 35
cagttcgcta tgacccatac a                                              21

<210> SEQ ID NO 36
<211> LENGTH: 21
<212> TYPE: DNA
<213> ORGANISM: Homo sapiens

<400> SEQUENCE: 36
tcttggacaa cacccagcag c                                              21

<210> SEQ ID NO 37
<211> LENGTH: 21
<212> TYPE: DNA
<213> ORGANISM: Homo sapiens

<400> SEQUENCE: 37
acatggatcc gagcccatgt a                                              21
```

<210> SEQ ID NO 38
<211> LENGTH: 21
<212> TYPE: DNA
<213> ORGANISM: Homo sapiens

<400> SEQUENCE: 38
aggaactttg ttgccacaat a                                    21

<210> SEQ ID NO 39
<211> LENGTH: 24
<212> TYPE: DNA
<213> ORGANISM: Homo sapiens

<400> SEQUENCE: 39
tctcactcaa agaagaagtt ggtg                                 24

<210> SEQ ID NO 40
<211> LENGTH: 24
<212> TYPE: DNA
<213> ORGANISM: Homo sapiens

<400> SEQUENCE: 40
tccagatcct gtgttctttt catt                                 24

<210> SEQ ID NO 41
<211> LENGTH: 25
<212> TYPE: DNA
<213> ORGANISM: Homo sapiens

<400> SEQUENCE: 41
tgtcttataa tgttctgcca atctg                                25

<210> SEQ ID NO 42
<211> LENGTH: 23
<212> TYPE: DNA
<213> ORGANISM: Homo sapiens

<400> SEQUENCE: 42
agttccgctc catagctgag aat                                  23

<210> SEQ ID NO 43
<211> LENGTH: 24
<212> TYPE: DNA
<213> ORGANISM: Homo sapiens

<400> SEQUENCE: 43
ggtgatgagc tttgagtttt cttt                                 24

<210> SEQ ID NO 44
<211> LENGTH: 24
<212> TYPE: DNA
<213> ORGANISM: Homo sapiens

<400> SEQUENCE: 44
atgtctgatg tactgtgtgc agtg                                 24

<210> SEQ ID NO 45
<211> LENGTH: 22
<212> TYPE: DNA
<213> ORGANISM: Homo sapiens

<400> SEQUENCE: 45
gttcccaaga accattcaag ag                                   22

<210> SEQ ID NO 46
<211> LENGTH: 24
<212> TYPE: DNA
<213> ORGANISM: Homo sapiens

<400> SEQUENCE: 46
taacttccct gatttaccttgagc                                        24

<210> SEQ ID NO 47
<211> LENGTH: 24
<212> TYPE: DNA
<213> ORGANISM: Homo sapiens

<400> SEQUENCE: 47
aagtccttgt ataaaaccca tgct                                       24

<210> SEQ ID NO 48
<211> LENGTH: 24
<212> TYPE: DNA
<213> ORGANISM: Homo sapiens

<400> SEQUENCE: 48
attgaccctg atgtggactt actc                                       24

<210> SEQ ID NO 49
<211> LENGTH: 24
<212> TYPE: DNA
<213> ORGANISM: Homo sapiens

<400> SEQUENCE: 49
ggtgatgagc tttgagtttt cttt                                       24

<210> SEQ ID NO 50
<211> LENGTH: 24
<212> TYPE: DNA
<213> ORGANISM: Homo sapiens

<400> SEQUENCE: 50
atgtctgatg tactgtgtgc agtg                                       24

<210> SEQ ID NO 51
<211> LENGTH: 23
<212> TYPE: DNA
<213> ORGANISM: Homo sapiens

<400> SEQUENCE: 51
gtgcacctga tgaatacatt gaa                                        23

<210> SEQ ID NO 52
<211> LENGTH: 24
<212> TYPE: DNA
<213> ORGANISM: Homo sapiens

<400> SEQUENCE: 52
ctgtattttt cccagatacc tgct                                       24

<210> SEQ ID NO 53
<211> LENGTH: 24
<212> TYPE: DNA
<213> ORGANISM: Homo sapiens

<400> SEQUENCE: 53

| | |
|---|---|
| cttggggcct acagtactgc ttat | 24 |

<210> SEQ ID NO 54
<211> LENGTH: 24
<212> TYPE: DNA
<213> ORGANISM: Homo sapiens

<400> SEQUENCE: 54

| | |
|---|---|
| tctccttggc atcattaaaa ctct | 24 |

<210> SEQ ID NO 55
<211> LENGTH: 24
<212> TYPE: DNA
<213> ORGANISM: Homo sapiens

<400> SEQUENCE: 55

| | |
|---|---|
| ctgtggtttt ggtcttagga actt | 24 |

<210> SEQ ID NO 56
<211> LENGTH: 24
<212> TYPE: DNA
<213> ORGANISM: Homo sapiens

<400> SEQUENCE: 56

| | |
|---|---|
| caaaatctta agctgctggg tatt | 24 |

<210> SEQ ID NO 57
<211> LENGTH: 24
<212> TYPE: DNA
<213> ORGANISM: Homo sapiens

<400> SEQUENCE: 57

| | |
|---|---|
| ctgtggtttt ggtcttagga actt | 24 |

<210> SEQ ID NO 58
<211> LENGTH: 24
<212> TYPE: DNA
<213> ORGANISM: Homo sapiens

<400> SEQUENCE: 58

| | |
|---|---|
| ttaatggaat cagccaaaat ctta | 24 |

<210> SEQ ID NO 59
<211> LENGTH: 24
<212> TYPE: DNA
<213> ORGANISM: Homo sapiens

<400> SEQUENCE: 59

| | |
|---|---|
| agtcttccac tgcacacagt acat | 24 |

<210> SEQ ID NO 60
<211> LENGTH: 22
<212> TYPE: DNA
<213> ORGANISM: Homo sapiens

<400> SEQUENCE: 60

| | |
|---|---|
| caactgaacc caaacctcat tc | 22 |

<210> SEQ ID NO 61
<211> LENGTH: 24
<212> TYPE: DNA
<213> ORGANISM: Homo sapiens

<400> SEQUENCE: 61

```
ctgtggtttt ggtcttagga actt                                          24

<210> SEQ ID NO 62
<211> LENGTH: 24
<212> TYPE: DNA
<213> ORGANISM: Homo sapiens

<400> SEQUENCE: 62
aaaatcttaa gctgctgggt attg                                          24
```

PHENYLALANINE HYDROXYLASE GENE VARIANTS, AND AMINO ACID AND PTERIN HOMEOSTASIS, IN THE DEFINITION, DETECTION, TREATMENT AND PREVENTION OF PSYCHOTIC, MOOD AND PERSONALITY DISORDERS

This application is a divisional application of U.S. application Ser. No. 09/253,025, filed Feb. 19, 1999 now U.S. Pat. No. 6,200,758.

GOVERNMENT INTERESTS

Part of the work performed during the development of this invention utilized U.S. Government Funds under Grant No. R01-44153 from the National Institute of Mental Health. The government may have certain rights in this invention.

FIELD OF THE INVENTION

The Inventor has developed and successfully applied a metabolic model of phenylalanine (Phe) metabolism to treatment development for neurological disorders, both to those seen only in psychiatric patients, and to those seen in the general population (U.S. Pat. No. 5,393,784; U.S. Pat. No. 5,670,539, allowed application U.S. application Ser. No. 08/545,095). The treatment method relates to a medical food product which has been clinically proven to reduce the availability of Phe to the central nervous system. The instant invention applies the Phe metabolism model to define and develop treatments to the genetics of psychotic, mood and personality disorders based on the results of (a) DNA analysis of the phenylalanine hydroxylase (PAH) gene, and (b) Phe dosing studies, in 124 patients with these disorders.

The PAH enzyme catalyzes the conversion of Phe to tyrosine (precursor of the amine neurotransmitter, dopamine), and deficient activity of this enzyme leads to increased plasma levels of Phe. Phe, as an indirect precursor of dopamine and noradrenaline, supports their synthesis at low plasma concentrations while at higher concentrations, it inhibits the synthesis of these two neurotransmitters in addition to serotonin. Thus plasma Phe levels play an important role in modulating neurotransmitter synthesis.

A model for Phe metabolism is valuable in the study of psychotic, mood and personality disorders (a) because of the role of Phe in amine neurotransmitter synthesis, (b) the suspected role of neurotransmitter function in these disorders, and (c) the fact that the limited treatment success that has been seen in these disorders is from agents that regulate neurotransmitter synthesis. Further, the acute sensitivity of the brain to higher than normal levels of Phe and its metabolites that occurs with deficiencies of PAH activity is well exemplified by the mental retardation, seizures, spasticity and EEG irregularities seen in phenylketonuria, a hyperphenylalanemia caused by deficient or absent PAH activity.

The psychotic disorders extract the greatest cost to the patient, family members, and to society at large. The most prevalent of the psychotic disorders both in the DNA study subject sample of the present invention and the general population is the disorder of schizophrenia. Schizophrenia is the most serious and the most treatment resistant of the disorders. It is heterogeneous in expression, etiology, and pathophysiology, with sex often being a defining variable. The disorder is known to have a complex pattern of inheritance indicative of interactions among multiple genes and environmental factors and has been difficult to analyze at a genetic level. The present invention relates to methods of identifying and methods of treating the psychotic disorder of schizophrenia, though the invention is applicable to the entire group of psychotic, mood and personality disorders.

DNA analyses of the PAH gene in the study sample have revealed significant associations between the disorder of schizophrenia and both a novel missense mutation (K274E) and novel polymorphism (L321L). There was a statistical association between the presence of these two variants in the study sample, and all persons with either of these variants were of African-American ethnicity. The K274E missense mutation results in a lysine to glutamic acid substitution at amino acid 274, the substitution of which may cause changes in the physical and chemical properties of the PAH protein. The physiological effect of the mutation may be also be relevant to schizophrenia since the mutation is located in a region considered to be involved in the binding of tetrahydrobiopterin ($BH_4$). $BH_4$ is the cofactor for Phe, tyrosine and tryptophan hydroxylases, all of which are required for the synthesis of the amine neurotransmitters dopamine, noradrenaline, and serotonin. These results suggest that the mutation may be relevant to the pathophysiology of schizophrenia.

Analysis of two-hour post Phe dose plasma Phe and tyrosine levels in the DNA study sample demonstrates (a) significantly higher Phe plasma levels, and (b) significantly less conversion to tyrosine, for those with the K274E mutation, indicating reduced catabolism of Phe for that group. In addition, differences in plasma levels for neopterin, biopterin and neopterin/biopterin ratio were observed between patients with and without the mutation, suggesting that increased synthesis of $BH_4$ may be associated with the K274E mutation. The increase in $BH_4$ synthesis may be a homeostatic response to reduced levels of PAH activity.

The effect of the novel L321L polymorphism on PAH enzyme activity is not known although the L321L polymorphism was found to be associated with schizophrenia and the K274E mutation. Studies of the variant may include investigations of DNA methylation and/or RNA splicing, stability or utilization. The significance of the L321L polymorphism is supported by the observation that patients with this polymorphism had significantly higher two-hour post Phe dose Phe plasma levels, and significantly less conversion to tyrosine, indicating reduced catabolism of Phe.

The nationally stated goal of the field of genetic research in psychotic, mood and personality disorders is to identify mutations that confer susceptibility to illness and that have predictable and understandable pathophysiological effects that may be related to these disorders. The present invention is a unique, hypothesis-driven approach toward meeting the goals of the field with (a) the discovery of a novel missense mutation and a novel polymorphism on a gene related to neurotransmitter synthesis in persons with psychotic, mood and personality disorders, (b) the discovery of a statistically significant association between the presence of these two variants, (c) the discovery of a statistically significant association between these two novel variants and the disorder of schizophrenia, (d) the discovery of a plasma dose response which supports significant physiological effects for the K274E mutation and L321L polymorphism and implicates these variants in the reduced catabolism of Phe, and (e) the discovery of a significant effect for the mutation in the increased synthesis of $BH_4$. Further, the ethnic homogeneity for the two novel PAH variants associated with schizophrenia improves the prospects of making a meaningful contribution to the understanding the genetics of the complex disorder of schizophrenia. Ethnic considerations are of critical importance in genetic studies. For example, in patients with schizophrenia, significant differences were observed between persons of African and European descent with respect to heterozygosity and the number of alleles per marker, whereas in patients with Alzheimer's Disease, the APOE-e4 allele is consistently associated with a greater risk for the disease in Caucasians but not in African-Americans.

Treatment of the disorder of phenylketonuria is an example where early detection and therapeutic intervention has made a significant impact on the overall cost to society. The deleterious central nervous system effects of that disorder, also caused by mutations and polymorphisms on the PAH gene, have been significantly diminished in the western world because of newborn screening of Phe plasma levels. Infants with high levels of Phe are placed on a Phe-restricted diet, and as a direct consequence of such dietary restriction the central nervous system is protected from severe consequences of high plasma Phe such as mental retardation. The association of the novel K274E mutation and L321L polymorphism with schizophrenia in African-Americans in combination with pedigree analysis may also have enormous public health benefits with respect to the treatment of the disorder schizophrenia.

BACKGROUND OF THE INVENTION

The phenylalanine hydroxylase enzyme catalyzes the conversion of the large neutral amino acid phenylalanine (Phe) to tyrosine, which is the rate-limiting step in the catabolism of Phe. The brain is highly sensitive to levels of Phe, and deficiencies in the PAH enzyme may result in excess levels of Phe or hyperphenylalanemia. Deficiencies in PAH enzyme activity may range from classical PKU and its potential for severe central nervous system dysfunction (mental retardation), to moderate elevations in plasma Phe with no known clinical consequences. A deficiency in PAH enzyme activity is the most common cause of hyperphenylalanemia, with 99% of the mutant alleles mapping to the PAH gene and the remainder mapping to several genes involved in the synthesis and recycling of tetrahydrobiopterin ($BH_4$), the cofactor in the hydroxylation reaction (Scriver C R, "Whatever happened to PKU?", Clin. Biochem., 1995, 28: 137–144). The human PAH gene spans 90 kb, is comprised of 13 exons, and has been localized to chromosome 12q24.1 (Lidsky A S et al., "Regional mapping of thephenylalanine hydroxylase gene and the phenylketonuria locus in the human genome", Proc Natl Acad Sci USA, 1985, 82:6221–6225; DiLela A G et al., "Molecular structure and polymorph map of the human phenylalanine hydroxylase gene", Biochemistry, 1986, 25:743–749). Structure/function analyses have identified a central catalytic domain which contains sites for substrate, iron and $BH_4$ cofactor binding, an N-terminal region with regulatory properties, and a C-terminal domain involved with intersubunit binding (Hufton S E et al., "Structure and function of the aromatic amino acid hydroxylases", Biochem J, 1995, 311:353–366; Waters P J et al., "In vitro expression analysis of mutations in phenylalanine hydroxylase: linking genotype to phenotype and structure to function", Hum Mutat, 1998, 11:4–17).

Although some studies have suggested that patients with PKU and heterozygotes for PKU might have an increased susceptibility for psychiatric disorders such as schizophrenia (Thompson J H, "Relatives of phenylketonuric patients", J Ment. Defic. Res. 1957; 1:67–78; Kuznersova L I, "Frequency and phenotypic manifestations of schizophrenia in the patients with phenylketonuria", Sov. Genet. 1974:554–555) this remains a topic of considerable controversy. Several investigations have found that there is no statistical evidence to demonstrate that the frequency of mental illness in PKU patients and their families exceeds levels in control populations (Perry T L et al., "The incidence of mental illness in relatives of individuals suffering from phenylketonuria or mongolism", J. Psychiatr. Res. 1966; 4:51–57; Blumenthal M D, "Mental illness in parents of phenylketonuric children:", J. Psychiatr. Res. 1967; 5:59–74; Larson C A and Nyman G E, "Phenylketonuria: mental illness in heterozygotes", Psychiatr. Clin. 1968; 1:367–374; Pietz J et al., "Psychiatric disorders in adult patients with early-treated phenylketonuria", Pediatrics, 1997, 99:345–350).

Investigations of Phe metabolism in psychiatric disorders are few and the findings are equivocal. Some studies have indicated that schizophrenic patients have higher levels of plasma Phe than control subjects (Poisner A M, "Serum phenylalanine in schizophrenia; biochemical genetic aspects", J. Nerv. Ment. Dis. 131:74–76, 1960; Bjerkenstedt et al., "Plasma amino acids in relation to cerebrospinal fluid monoamine metabolites in schizophrenic patients and healthy controls", Br. J. Psychiatry, 1985, 147:276–282; Rao M L et al., "Serum amino acids, central monoamines, and hormones in drug-naive, drug-free, and neuroleptic-treated schizophrenic patients and healthy subjects", Psychiatry Res. 1990, 34:243–257), while another reported no significant difference between the two groups (Szymanski H V et al., "Plasma phenylethylamine and phenylalanine in chronic schizophrenic patients", Biol. Psychiatry 1987; 22:194–198). The results for another index of Phe metabolism (the level of plasma Phe following a Phe challenge) have been similarly ambiguous, with a report from one group of investigators that post-challenge Phe levels were increased in schizophrenic patients compared to controls, which they subsequently failed to replicate (Wyatt R J et al., "Phenylethylmine (PEA) and chronic schizophrenia", Catecholamines: Basic and Clinical Frontiers, Usdin K., Kopin I J, Barchas J D, eds. New York: Raven Press, 1979; 1833–1835; Potkin S G et al., "Plasma phenylalanine, tyrosine, and tryptophan in schizophrenia" Arch. Gen. Psychiatry 1983; 40: 749–752).

Another aspect of the studies on Phe metabolism in schizophrenia have focused on phenylethylamine, which is produced in excess by a decarboxylase pathway in the absence or impairment of PAH activity. Phenylethylamine has been proposed to act as a neuromodulator via serotonin receptors (Boulton A A et al., "Phenylethylamine in the CNS: effects of monoamine oxidase inhibiting drugs, deuterium substitution and leisons and its role in the neuromodulation of catecholaminergic neurotransmission", J. Neural Transmission Suppl. 1990; 29: 119–129, Sloviter R S et al., "Serotonergic properties of b-phenethylamine in rats", Neuropharmacology 1981; 20: 1067–1072) and is of interest in schizophrenia research since it is a chemical congener of amphetamine, abuse of which produces a psychosis resembling paranoid schizophrenia (Snyder S H, "Amphetamine psychosis: a "model" schizophrenia mediated by catecholamines", Am J. Psychiatry 1973; 130: 61–67). Investigators have reported differences between schizophrenic patients and control subjects including differences between groups of schizophrenic subtypes, as measured by the level of phenylethylamine in body fluids (Szymanski H V et al., "Plasma phenylethylamine and phenylalanine in chronic schizophrenic patients", Biol Psychiatry 1987; 22: 194–198.69; Potkin S G et al., "Phenylethylamine (PEA) and phenylacetic acid (PAA) in the urine of chronic schizophrenic patients and controls", Psychopharmacol Bull 1980; 16-:52–54; Jeste D V et al., "Cross-cultural study of a biochemical abnormality in paranoid schizophrenia", Psychiatry Res. 1981; 5: 341–352; Yoshimoto S et al., "Urinary trace amine excretion and platelet monoamine oxidase activity in schizophrenia", Psyciatry Res. 1897; 21:229–236; O'Reilly R et al., "Plasma phenylethylamine in schizophrenic patients", Biol. Psychiatry 1991; 30:145–150; Fischer E et al., "Urinary elimination of phenethylamine", Biol Psychiatry 1972; 5: 139–147). These studies on phenylethylamine, though more numerous than those on Phe, have been considered particularly problematic because of the trace amine status of phenylethylamine (small amounts, rapid transit through systems, unstable) which has resulted in technological difficulties in measurement of the amino and lack of conformity in values across studies.

The study of Phe metabolism is the most limited in psychiatric disorders other than schizophrenia. In patients with endogenous depression, unipolar depression or bipolar syndrome, the response to a Phe challenge was indistinguishable from that in control subjects (Pratt R T C et al., "Phenylalanine tolerance in endogenous depression", Brit. J. Psychiat., 1963, 109:624–628; Targum S D et al., "Screening for PKU heterozygosity in bipolar affectively ill patients", Biol. Psych., 1979, 14:651–655; Gardos G et al., "The acute effects of a loading dose of phenylalanine in unipolar depressed patients with and without tardive dyskinesia", Neuropsychopharmacology, 1992, 6:241–247).

Only two investigations have examined the PAH gene and schizophrenia and both have produced negative findings. The first of these screened for two specific mutations in the PAH gene (the putative null mutations R408W and IVS 12nt1) in schizophrenics and normal controls. None of the schizophrenic subjects in the study were found to have these variants. It was thus concluded that neither of these genetic polymorphisms were associated with a predisposition to schizophrenia (Sobell J L et al., "Novel association approach for determining the genetic predisposition to schizophrenia: case-control resource and testing of a candidate gene", Am. J. Med. Genet. 1993; 48:28–35). The second study was a genome-wide search for schizophrenia susceptibility genes. The investigators failed to find a significant association between PAH and disease susceptibility (Shaw S H et al., "A genome-wide search for schizophrenia susceptibility genes", Am. J. Med. Genet. 1998; 81:364–376).

No other studies have found an association between the PAH locus on chromosome 12 in reference to psychiatric disorders. One publication describes an investigation of the relationship between schizophrenia and the phospholipase-A2 gene, the result of which was negative (Psychiatr Genet. 1995, 5:177–80; O-Malley M P et al. Linkage analysis between schizophrenia and the Darier's disease regionon 12q, Psychiatr Genet. 1996: 6:187–90).

The psychotic disorders are the most serious of the psychiatric illnesses and make up the bulk of the patients in the public sector extracting a major economic cost from society. Patients afflicted with psychosis suffer from symptoms such as delusions, hallucinations, disorganized speech and grossly disorganized or catatonic behavior. The disorders in this category are schizophrenia, schizophreniform disorder, schizoaffective disorder, brief psychotic disorder, delusional disorder, shared psychotic disorder, psychotic disorder due to a general medical condition, substance-induced psychotic disorder, psychotic disorder not otherwise specified (American Psychiatric Association: *Diagnostic and Statistical Manual of Mental Disorders,* Fourth Edition, Washington, D.C., American Psychiatric Association, 1994).

The most prevalent of these disorders is schizophrenia having a lifetime prevalence ranging from 0.5% to 1%, the particular symptoms of which are the following (American Psychiatric Association: *Diagnostic and Statistical Manual of Mental Disorders,* Fourth Edition. Washington, D.C., American Psychiatric Association, 1994):

1. Delusions—are erroneous beliefs that usually involve a misinterpretation of perceptions or experiences. Presecutory delusions are the most common; the person believes he or she is being tormented, followed, tricked, spied on, or subjected to ridicule. Referential delusions are also common; the person believes that certain gestures, comments, passages from books, newspapers, song lyrics or other environmental cues are specifically directed at him or her. Bizarre delusions are especially characteristic of schizophrenia. An example of a bizarre delusion is a person's belief that a stranger has removed his or her internal organs and has replaced them with someone else's organs without leaving any wounds or scars.

2. Hallucinations—auditory hallucinations are the most common and are experienced as voices that are perceived as distinct from the person's own thoughts. Pejorative or threatening voices are the most common. Most characteristic of schizophrenia are two or more voices conversing with one another or voices maintaining a running commentary on the person's thoughts or behaviors.

3. Disorganized thinking—formal thought disorder, loosening of associations; as manifested by speech that is disorganized enough to substantially impair effective communication; such as, derailment where the person slips off the track of a thought, answers to questions may be completely unrelated, speech may be so severely disorganized that it is incomprehensible as resembling a word salad.

4. Grossly disorganized behavior—problems may be seen in any form of goal-directed behavior, leading to problems performing activities of daily living. For instance, the person may be markedly disheveled, dress in an unusual manner (e.g., multiple overcoats on a hot day), show inappropriate sexual behavior (e.g., public masturbation), show childlike silliness, show unpredictable and untriggered agitation.

5. Catatonic motor behaviors—a marked decrease of reactivity to the environment which can reach to stupor, maintaining a rigid posture and resisting efforts to be moved, inappropriate or bizarre postures, or purposeless and unstimulated excessive motor activity.

6. Negative symptoms—persons face appears immobile and unresponsive with poor eye contact and reduced body language, speech is characterized by brief, laconic, empty replies, person has an inability to initiate and persist in goal-directed activities, and will sit for long periods of time and show no interest in participating in work or social activities.

The disorders in the category of Mood Disorders are; Major Depressive Disorder, Dysthymic Disorder, Depressive Disorder Not Otherwise Specified, Bipolar I Disorder, Bipolar II Disorder, Cyclothymic Disorder, Bipolar Disorder Not Otherwise Specified, Mood Disorder Due to a General Medical Condition, Substance-Induced Mood Disorder, Mood-Disorder Not Otherwise Specified (American Psychiatric Association: *Diagnostic and Statistical Manual of Mental Disorders,* Fourth Edition. Washington, D.C., American Psychiatric Association, 1994).

The disorders in the category of Personality Disorders are; Paranoid Personality Disorder, Schizoid Personality Disorder, Schizotypal Personality Disorder, Antisocial Personality Disorder, Borderline Personality Disorder, Histrionic Personality Disorder, Narcissistic Personality Disorder, Avoidant Personality Disorder, Dependent Personality Disorder, Obsessive-Compulsive Personality Disorder, Personality Disorder NOS (American Psychiatric Association: *Diagnostic and Statistical Manual of Mental Disorders,* Fourth Edition. Washington, D.C., American Psychiatric Association, 1994).

It was through the results of several independent studies in these patient groups, that the Phe metabolic model was developed and which forms the background of the invention. The model is based on the following established criteria in relation to the role of Phe in neurotransmitter synthesis.

The main factors determining the entry of Phe into the brain are its concentration in plasma, the concentration of the competing large neutral amino acids in plasma, and the activity of the blood-brain barrier transport system or L-system. The L-system, which competitively mediates the bi-directional flux of the neutral amino acids between the blood and brain, has a preferential affinity for the large neutral amino acids, with Phe having the highest affinity among them (Daniel P M et al. "Amino acid precursors of monoamine neurotransmitters and some factors influencing their supply to the brain" *Psychol. Med.* 1976; 6: 277–286; Pardridge W M and Choi T B, "Neutral amino acid transport at the human blood-brain barrier", *Federation Proceedings,* 1986, 45: 2073–2078). Due to the competition between amino acids for brain entry, higher concentrations of plasma Phe can result in lower brain availability of tyrosine and tryptophan. These latter amino acids serve as precursors in the synthesis of the neurotransmitters dopamine, serotonin and noradrenaline, all of which have been implicated in psychotic, mood and personality disorders. Further, an inhibitory effect of Phe and its metabolites (such as phenylethylamine and phenylacetic acid) on the activities of tyrosine hydroxylase, tryptophan hydroxylase, and DOPA decarboxylase further decreases the synthesis of dopamine, noradrenaline and serotonin (Caballero B and Wurtman R J, "Control of plasma phenylalanine levels" Ch. 1, In: Wurtman R J and Ritter-Walker, E, eds. *Dietary Phenylalanine and Brain Function.* Boston: Birkhauser, 1988; 3–12; Lehnert H and Wurtman R J, "Amino acid control of neurotransmitter synthesis and release: physiological and clinical implications" *Psychotherapy & Psychosomatics,* 1993; 60: 18–32; Maher T, "Effects of phenylalanine on the synthesis, release and function of catecholaminergic systems" in *Amino Acids in Psychiatric Disease.* Washington: American Psychiatric Press, Inc., 1990; 131–142; Scriver C R and Rosenberg L E, "Phenylalanine" Ch. 15, In: Schaffer Al, eds. *Amino Acid Metabolism and its Disorders.* Philadelphia, 1973; 290–337). Thus the integrity of the Phe metabolic system is critically important in the function of neurotransmitter systems thought to be involved in these disorders. Higher plasma Phe levels have been shown to be significantly associated with lower central nervous system levels of tyrosine and trytophan in a sample of schizophrenics (Bjerkenstedt L et al. "Plasma amino acids in relation to cerebrospinal fluid monoamine metabolites in schizophrenic patients and healthy controls" *Br. J. Psychiatry,* 1985; 147: 276–282).

The Phe metabolic model was initially developed to allow for the development of treatment strategies for a neurological disorder, tardive dyskinesia (TD). This disorder is a side effect of neuroleptic treatment (drugs that block dopamine function, and more recently in the atypical form also block serotonin function) which has been the primary treatment for schizophrenia, and the other psychoses. It was suggested that the symptoms of the disorder were due to a dopaminergic supersensitivity brought on by years of treatment with dopamine-blocking drugs. More recent studies have suggested that lifelong reduced dopamine synthesis due to chronically higher levels of plasma Phe may increase the vulnerability to the development of TD. These drugs are also used in the treatment of mood and personality disorders. Persons with mood disorders have been shown to have a particular vulnerability to the development of TD when treated with neuroleptics. All three groups of these disorders are believed to at least partially respond to treatment with medications that regulate amine neurotransmitter synthesis.

A summary of the studies which form the core of the Phe metabolic model are as follows:

1. The association of hyperphenylalanemia with TD (Study 1). A point prevalence study of TD (n=211) in a mentally retarded population showed that phenylketonuria, a severe hyperphenylalaninemia, was a significant risk factor for the presence of TD. These data suggested that high plasma Phe was associated with the development of TD (Richardson, M. A. et al., "The prevalence of tardive dyskinesia in a mentally retarded population" *Psychopharmacol. Bull.,* 1986; 22: 243–249).

2. Protein challenge given to schizophrenic men with and without TD. A dietary challenge in the form of a high-protein meal (Phe=3.6% of total protein, branched chain amino acids (BCAA=19.6% of total protein) was administered to 53 male schizophrenics (Study 2). The findings were:

(a) Alteration of protein kinetics in men with TD. Data analyses established that the post-challenge plasma Phe level and post-challenge Phe/large neutral amino acid ratio were significantly higher in patients with TD and were significant predictors of TD status in male schizophrenic patients, independent of age. The ratio corrects for the competition of the other large neutral amino acids with Phe at the blood-brain barrier (Richardson, M. A. et al., "The plasma phenylalanine/large neutral amino acid ratio: a risk factor for tardive dyskinesia" *Psychopharmacol. Bull.,* 1989; 25: 47–51; Richardson, M. A. et al., Comment on 'The ratio of plasma phenylalanine to other large neutral amino acids is not a risk factor for tardive dyskinesia' *J. Psychopharm.,* 1993; 7: 2; Richardson, M. A. et al., "Tardive dyskinesia and phenylalanine metabolism: risk-factor studies" Ch. 13, in: Yassa, R. et al., eds. *Neuroleptic-Induced Movement Disorders.* Cambridge: Cambridge University Press, 1997: 161–174; Richardson, M. A. et al., "Plasma phenylalanine: A measure of tardive dyskinesia vulnerability in schizophrenic males" Chap.7, in: Richardson, M. A., eds. *Amino Acids in Psychiatric Disease.* Washington, D.C.: American Psychiatric Press, 1990: 143–160).

(b) Unexpected total remission of TD symptoms. More than half of the patients with TD had either a complete remission of their TD symptoms or a minimum 50% decline in symptoms two hours after the protein meal. Plasma analyses demonstrated that there were significantly lower Phe/large neutral amino acid and tyrosine/large neutral amino acid ratios and significantly higher branched chain amino acid/large neutral amino acid ratios in the group of patients who had a remission, as compared with those who did not. The authors hypothesized that the protein challenge comprised of high branched chain amino acid content, may have reduced the availability of Phe and tyrosine to the central nervous system, effecting the dramatic symptom remission (Richardson, M. A. et al., "Phenylalanine to serotonin to tardive dyskinesia: A new model", *Proceedings of the 2nd International Symposium on Serotonin, from Cell Biology to Pharmacology and Therapeutics,* Houston, Tex. Sep. 15–18, 1992; Richardson, M. A. et al., "A dietary intervention decreases tardive dyskinesia symptoms" *Am. Psychiatr. Assoc.,* 149th Annual Meeting, New York, N.Y. 1996; 0:194).

3. Alteration of Phe kinetics in men with ID (Study 3). The study hypothesis, that TD would be associated with significantly higher plasma Phe indices (absolute plasma Phe level, plasma Phe/large neutral amino acid ratio) two hours after a Phe challenge, was verified for the male participants in the study (N=209; total N=312). The altered kinetics of Phe in men with TD indicated that there was a greater availability of Phe to the brains of these men. These data suggest that the disorder may be related to the effects of this greater availability. Such effects could be the direct neurotoxic effects of Phe and its metabolites and/or the modulating effects of these compounds on the synthesis of the monoamine neurotransmitters (Richardson, M. A. et al., "Tardive dyskinesia and phenylalanine metabolism: risk-factor studies. Ch. 13, in: Yassa, R. et al., eds. *Neuroleptic-Induced Movement Disorders.* Cambridge; Cambridge University Press, 1997: 161–174; Richardson, M. A. et al., "Phenylalanine metabolism: Sex and Age issues" *Schizophrenia Research,* 1996; 18: 149; Richardson M A, Reilly M A, Read L L, Flynn C J, Suckow R F, Maher T J, Sziraki I: Phenylalanine kinetics are associated with tardive dyskinesia in men but not in women. *Psychopharmacology,* in press).

4. Treatment of TD with a dietary supplement of the BCAA (Study 4). Clinical trials were conducted to determine whether a drink containing exactly the same amount and proportion of the BCAA as was in the protein challenge meal in Study 2 (given three times a day for two weeks) would decrease TD symptoms (Richardson M A, Bevans M L, Weber J B, Gonzalez J J, Flynn C J, Read L L, Suckow R F, Maher T J: Branched chain amino acids decrease tardive dyskinesia symptoms. Psychopharmacology, in press; (Richardson, M. A. et al., "A dietary intervention decreases tardive dyskinesia symptoms" *Am. Psychiatr. Assoc.,* 149th Annual Meeting, New York, N.Y. 1996; 0: 194; Richardson, M. A. et al., "TD symptom decreases with regulation of plasma large neutral amino acids. *Schizophrenia Research* 1997; 24:272; Richardson, M. A. et al., "TD symptom decreases with regulation of plasma large neutral amino acids" *Abstracts, 16th International Congress of Nutrition,* Montreal, Canada 1997; 0:42). A statistically significant decrease in the level of TD symptoms was observed for the sample. The symptom changes were also clinically significant in that 6 of the 9 subjects had symptom decreases of at least 58%, with all subjects having a decrease of at least 38%. Branched chain amino acid administration increased plasma branched chain amino acid concentrations and branched chain amino acid/large neutral amino acid ratios, and decreased plasma levels and large neutral amino acid ratios of Phe, tyrosine, and tryptophan. Analyses indicated a strong significant correlation between the percent increase in the plasma branched chain amino acid values at the first administration and the percent improvement in TD over the trial in eight of the nine subjects. The study findings suggested that the decrease in TD symptoms was modulated by a decrease in the brain uptake of Phe, a decrease in neurotransmitter synthesis, and/or the increase of the branched chain amino acid and decrease of aromatic amino acids in the periphery.

5. Placebo-controlled trial for the BCAA as a treatment for TD in adult men (Study 5). A placebo-controlled trial of the BCAA drink for the treatment of TD in men was designed to eliminate ineffective doses. For a response criteria of 50% decrease in symptoms, no responders were observed at the placebo dose, or at a low dose. A 17% rate of responders was observed at the mid-dose, and a 50% rate of responders in the high dose group. The trend in these data suggested a significant active versus placebo group response.

6. Pilot trial of the BCAA in the treatment of dyskinesias in neuroleptic-treated children and adolescents 9 (Study 6). Substantial decreases in symptoms for dyskinesias were seen in five out of six adolescents treated for two weeks. The decreases ranged from 37% to 68%. Two adolescent boys went into roll-on treatment periods. The percent decrease in symptoms was accelerated in the longer treatment periods. One subject who showed a 50% decrease after two weeks of treatment showed a 94% decrease after 31 days, and a second subject who showed a 54% decrease after two weeks of treatment showed a 74% decrease after 54 days of treatment.

7. DNA analysis of the PAH gene in psychiatric patients and controls (Study 7). The association between TD and diminished Phe kinetics in combination with the reduction of TD symptoms following a medical food product, led to the screening of the PAH gene in patients with psychotic, mood and personality disorders both with and without TD. The study hypothesis was that PAH variants may cause modest but significant changes in PAH activity that result in differences in Phe kinetics following a dietary Phe dose. It was further hypothesized that PAH variants may also have long term effects including predisposition to TD and psychotic disorders The findings of this study comprise the object of the invention, which is presented in the Field of Invention, and described in the Detailed Description and Examples 1–7.

SUMMARY OF THE INVENTION

Central to the present invention is the discovery of (a) point mutations and polymorphisms of the PAH gene that differ from the predominant wild-type PAH gene, in persons diagnosed with Psychotic, Mood or Personality Disorders, (b) significant associations between these sequence altered forms of the PAH gene and the presence of one of the Psychotic Disorders, Schizophrenia, and (c) significant associations between the sequence altered forms of the PAH gene and enzyme, and experimental plasma responses indicative of reduced function of the enzyme.

The invention includes the detection of sequence altered forms of the PAH gene, in order to define pathophysiological subtypes of the Psychotic, Mood or Personality Disorders, particularly Schizophrenia that would respond to treatment or prevention with a class of amino acid products already developed and patented by the Inventor. The epidemiology of these PAH variants in the Inventor's work suggests that certain of these variants will be particularly relevant for persons of African ethnicity. These subtypes can be defined by dual markers; one, the presence of PAH gene variants, and/or, two, an experimental plasma reponse to a Phe dose defining an altered function of the PAH enzyme. For persons already afflicted with Psychotic, Mood or Personality Disorders these data will allow for the definition of a pathophysiological subtype that will respond to treatment with one or more of a range of treatments. For their relatives, without psychiatric disease, these data will allow for detection of those relatives who have an increased susceptibility to the development of such psychiatric disease, and thus would be candidates for preventative treatment with the same range of treatments as.

The invention includes a method for detecting the presence of DNA encoding variants of the PAH gene, which comprises isolating DNA and amplifying a region of the DNA that encodes a nucleotide substitution, wherein a nucleotide substitution indicates the presence of a mutation or a polymorphism. The amplification step comprises a polymerase chain reaction involving specific primers complementary to regions throughout the PAH gene. Primer pairs are designed for either DGGE or SSCP methods of gradient gel filtration.

DETAILED DESCRIPTION OF THE INVENTION

The present invention is related to the discovery of two mutations and ten polymorphisms on the PAH gene in a group of 124 psychiatric patients carrying the diagnoses of Psychotic, Mood or Personality Disorders. The PAH enzyme catalyzes the conversion of the large neutral amino acid, Phe to tyrosine, which is the rate limiting step in the catabolism of Phe. The brain is highly sensitive to levels of Phe and deficiencies in the PAH enzyme can result in excess levels of Phe (hyperphenylalanemia) with a wide range of phenotypes, the most serious being the mental retardation of classical PKU. Phe, as an indirect precursor of the neurotransmitters dopamine and noradrenaline, supports their synthesis at low plasma concentrations while at higher concentrations it inhibits the synthesis of these two neurotransmitters and that of a third, serotonin. Thus plasma Phe levels play an important role in modulating neurotransmitter synthesis. The amine neurotransmitters (dopamine, noradrenaline, and serotonin) have long been considered to be relevant to the pathophysiology of the Psychotic, Mood and Personality Disorders, and the regulation of these neurotransmitters has been the goal of the medications developed to treat most of these disorders.

One of the PAH mutations (K274E), found in the Inventor's study, is novel, while the other mutation (A403V) is known to cause hyperphenylalanemia. Four polymorphisms are novel (IVS6nt-7, N133N, L321L, N426N) while the remaining six (IVS2nt19, IVS3nt-22, Q232Q, V245V, L385L, Y414Y) were already known. The K274E and the L321L variants were significantly associated with Schizophrenia (a Psychotic Disorder) and with each other, while the IVS2nt19 polymorphism showed a trend to a significant association with the disorder.

Ethnic considerations, particularly African-American status, were important in the data set since (a) all persons with the K274E and L321L variants (which were associated with schizophrenia) were African-Americans, (b) three of the five novel variants (K274E, L321L, N426N) was significantly associated with being African-American, and (c) for one of the other novel variants (IVS6nt-7) all Schizophrenics with this variant were African-American. The one person in the data set with the A403V mutation was Caucasian and schizophrenic. Caucasian ethnic status was significantly associated with three known polymorphisms (IVS3nt-22, Q232Q, V245V). Ethnic status has been a critical variable in uncovering the genetic background to disease expression, for instance in the case of Alzheimer's Disease, the APOE-e4 allele is consistently associated with a greater risk for the disease in Caucasians but not in African-Americans. In Schizophrenia, significant differences have been seen between those of African and European descent in heterozygosity and marker allele frequency, leading investigators to separate these groups for genetic analysis.

Taking a unique approach to the analysis of the genetics involved in the Phe metabolic pathway, all subjects who participated in the DNA study performed by the Inventor were exposed to a physiological experimental situation to determine the efficiency of PAH activity. Phe, the amino acid catabolized by PAH, was given to subjects in a 100 mg/kg body weight dose. Blood samples for large neutral amino acid analysis were collected fasting and two hours after the Phe dose administration in order to be able to test the kinetics of Phe. Fasting blood samples were also collected for analysis of neopterins and biopterins which are indicators of $BH_4$ synthesis and utilization. $BH_4$ is critical for amine neurotransmitter synthesis in its capacity as a cofactor for PAH (Phe to tyrosine), tyrosine hydroxylase (tyrosine to dopamine), and tryptophan hydroxylase (tryptophan to serotonin).

Information which is critical to the utilization of the Invention and unique to the field of the genetics of Psychotic, Mood and Personality Disorders was defined by the analysis of the results of the plasma assays performed. Patients with the K274E mutant protein were seen to have a significantly reduced ability to convert the ingested Phe to tyrosine, and a significantly lower neopterin/biopterin ratio (indicative of an increase in $BH_4$ synthesis). Persons with the L321L polymorphism also showed significantly reduced ability to convert the ingested Phe to tyrosine. The person with the A403V mutation showed a similar metabolic profile but to a more pronounced degree which is consistent with her hyperphenylalanemic status.

In Examples 8 and 9 the PAH K274E mutation is used as a marker to define a subtype of schizophrenia and susceptibility to schizophrenia in those of African-American ethnicity. The subtype of schizophrenia defined by the presence of this mutation will be one whose symptoms respond to treatment that lowers the availability of Phe to the brain. For first and second degree relatives of schizophrenics, the presence of the PAH K274E mutation and/or altered plasma values of Phe, tyrosine, biopterin and neopterin will define persons who may be susceptible to the development of schizophrenia.

The Inventor has patented a medical food product composed of the branched chain amino acids (BCAA) (U.S. Pat. No. 5,393,784) for use in TD. The BCAA formulation that has been used is valine: isoleucine: leucine at a ratio of 3:3:4. This product has been clinically proven to decrease Phe availability to the brain. The BCAA product can be used to treat schizophrenic symptoms in those persons with the K274E mutation. Additionally, the BCAA (in the above ratio) can be used to prevent the development of Schizophrenia in their first and second degree relatives.

Elaboration of methods proposed in Example 8 are as follows:

1. DGGE Kit. Kits will be useful for the detection of sequence variants in the PAH gene. The kit will be comprised of a set of 14 primer oligonucleotides, and an information sheet containing the primer sequences and the wild-type phenylalanine hydroxylase gene sequence.

Sequence variants will be identified following extraction of DNA from blood cells or other biological samples collected from subjects for screening. Extraction of the DNA can be performed by methods known in the field of art. The extracted DNA will be subjected to PCR amplification of fragments covering the PAH variants of Example 1, followed by denaturing gradient gel electrophoresis (DGGE). The kit will provide the primers for the PCR amplification that will correspond to SEQ ID Nos. 3, 4, 7, 8, 11–14, 17, 18, 21–24. The PCR-amplified DNA fragments will be fractionated on polyacrylamide gels with urea and/or formamide gradients. After electrophoresis, band patterns will be visualized using a phosphoimager or other visualization system. The primer sequences and methods have been previously described (Guldberg P and Guttler F, "A simple method for identification of point mutations using denaturing gradient gel electrophoresis", *Nucleic Acids Res.*, 1993, 21: 2261–2; Guldberg P et al., "Molecular analysis of phenylketonuria in Denmark: 99% of the mutations detected by denaturing gradient gel electrophoresis", *Genomics*, 1993, 17 141–6; Guldberg et al., "Mutational spectrum of phenylalanine hydroxylase deficiency in Sicily: implications for diagnosis of hyperphenylalanemia in Southern Europe", *Hum Mol Genet,* 1993, 2: 1703–1707; Guldberg P et al., "Phenylalanine hydroxylase gene mutations in the United States: report from the Maternal PKU Collaborative Study", *Am J. Hum Genet.,* 1996, 59: 84–94).

2. SSCP kit. The single stranded conformation polymorphism (SSCP) method is the preferred method of detection for known gene sequence variants at the single base-pair level in a clinical laboratory environment (Orita-M et.al, "Detection of polymorphisms of human DNA by gel electrophoresis as single-stranded conformation polymorphisms", *Proc Natl Acad Sci USA,* 1989, 86: 2766–2760). For detection of the PAH gene sequence variants described in this Invention, a kit will be comprised of a set of 24 primer oligonucleotides corresponding to SEQ ID Nos. 39–62. Also included will be PCR products from control individuals who are homozygous and heterozygous for each PAH variant targeted, to serve as electrophoretic mobility standards. In addition the kit will include an information sheet containing the primer sequences and a list of the PAH variant sequences detected by the kit.

3. Immunological detection. Diagnostic kits used to detect the K274E mutation by immunological detection may include a solid support capable of binding the PAH/K274E protein isoform, and further include one or more antibodies which are allele-specific and whose binding to the specific allele can be detected by the generation of a signal or the detection of a label. Other versions of a diagnostic kit include a kit comprising an allele-specific antibody attached to a solid support, capable of binding an antigen which is the PAH/K274E allele, and a means for detection of the antibody-antigen complex.

Alternative uses of the Invention to those proposed in Examples 8 and 9 are as follows:

1. The L321L variant is significantly associated with schizophrenia and with the presence of the K274E mutation, and persons with this mutation show a significantly reduced ability to convert ingested Phe to tyrosine. The presence of this variant can also be used to define a subtype of persons with Schizophrenia whose symptoms may respond to treatment with the BCAA. This variant can also be used to define first and second degree relatives of schizophrenics who will then be tested as described in Example 9 by administration of a 100 mg/kg dose of Phe. Post dose plasma values of Phe, and tyrosine, and percent change values from fasting to post dose will be studied for both amino acids. If test results are within the parameters listed in Example 9 then these relatives may be defined as susceptible to developing Schizophrenia. The definition may be used to qualify these relatives as candidates for prophylactic treatment with the BCAA.

2. For the three other novel polymorphisms (IVS6nt-7, N133N, N426N), patients with these variants can be tested as described in Example 9 by administration of a 100 mg/kg dose of Phe. Post dose plasma values of Phe, and tyrosine, and percent change values from fasting to post dose can be studied for both amino acids. If test results are within the parameters listed in Example 9 then these patients may be candidates for treatment with the BCAA.

3. The known IVS2nt19 polymorphism showed a trend for an association with schizophrenia, but showed a significantly lower post Phe dose level of Phe and a significantly lesser response to a 100 mg/kg Phe dose than in patients without the polymorphism. This suggests a dysregulation related to the psychosis that might respond to the use of administered Phe. The Inventor has patented the use of Phe in movement disorders (U.S. Pat. No. 5,670,539; allowed application U.S. application Ser. No. 08/545,095).

4. The presence of the A403V mutation in patients with schizophrenia may serve as a marker for a BCAA treatment response (aimed at reducing Phe availability to the brain). The first and second degree relatives of a person with this mutation and schizophrenia should be screened for the presence of this mutation. If present, they should then be tested to see if they have Phe and tyrosine plasma values two-hours subsequent to a 100 mg/kg Phe dose comparable to those seen in this patient (see Example 5.) or within the parameters presented in Example 9, then these relatives may be defined as susceptible to developing Schizophrenia. The definition may be used to qualify these relatives as candidates for prophylactic treatment with the BCAA.

5. Where a linkage between any of the two mutations and ten polymorphisms, and the presence of schizophrenia in African-American pedigree studies (See Example 8) has been demonstrated, then those variants can be used to define both a subtype of schizophrenia in patients with the disorder and susceptibility to schizophrenia in relatives who have not yet shown symptoms of the disorder. Both these groups would be candidates for treatment with the BCAA.

6. Any persons with Psychotic, Mood and Personality Disorders who are shown to have any of these two mutations and ten polymorphisms in the PAH gene can be tested as described in Example 9 by administration of a 100 mg/kg dose of Phe. Post dose plasma values of Phe, and tyrosine, and percent change values from fasting to post dose can be studied for both amino acids. If test results are within the parameters listed in Example 9 then treatment with BCAA can be offered. For disorders such as Major Depressive Disorder where deficits in tyrosine may be seen, consideration will be given to treatment with tyrosine. The Inventor has patented the use of tyrosine in movement disorders (U.S. Pat. No. 5,670,539; allowed application U.S. application Ser. No. 08/545,095).

7. Persons with Psychotic, Mood and Personality Disorders, in the absence of (a) the determinations of PAH variants, (b) plasma responses to a Phe dose in Phe and tyrosine levels, or (c) biopterin and neopterin levels, would be seen as candidates for treatment with the BCAA if the treatment mechanism of action of these amino acids is considered appropriate for their disorder.

Further details regarding this invention are presented but are not limited to the Examples.

EXAMPLES

Example 1

Identification of PAH Gene Sequence Variants in Patient and Control Subjects

A genetic screen of PAH in a population of 124 public sector psychiatric patients and 46 normal control subjects was conducted to investigate the hypothesis that psychiatric patients have PAH mutations which could have long term effects including predisposition to psychiatric disorders. For patient subjects, all residents and newly admitted patients to a state psychiatric center and two state-run community residential programs were screened for inclusion in the study during a two-year period. Intensive screening methods insured that all patients of each facility had an equal chance of entering the study. Exclusion criteria arose from concerns of diagnostic homogeneity and patient safety, they were; a primary chart diagnosis of an organic mental disorder or mental retardation, diabetes, current use of antiseizure medication, or a seizure within the prior two years. Informed consent was obtained from all subjects in accordance with N. S. Kline Institute for Psychiatric Research and Rockland Psychiatric Center of the New York State Office of Mental Health, community treatment providers, Institutional Review Board guidelines and regulations. Normal control subjects were recruited from the community, employees and relatives of employees of the Research Institute and Psychiatric Center. A lifetime psychiatric diagnosis (using DSM-III-R criteria) was also determined for each patient based both on clinical data collected from current and previous admissions, clinical status evaluations (Brief Psychiatric Rating Scale, Hamilton Rating Scale for Depression and the Mini-Mental State Exam) and diagnostic interviews performed by the study team.

In Table 1 the control population of 46 subjects has been classified by gender and ethnicity, and the patient population of 124 subjects has been classified by gender, psychiatric diagnosis, ethnicity and TD prevalence. In the psychiatric diagnosis parameter, the category of "other diagnosis" includes; Psychosis, not specified (n=5), Personality Disorder (n=4), Organic Disorders (n=4), Substance-induced Psychotic Disorder (n=3).

The patient and control group profiles showed similar representation by gender and by ethnic status. Within the patient sample, the diagnosis of schizophrenia was most prevalent, accounting for 45% of the patient group. Table 2 shows diagnosis by ethnic status within the patient group. Those of African-American and Hispanic ethnic status showed higher rates of schizophrenia than the Caucasian group; this difference showed a trend toward statistical significance (Chi-square=5.362; p=0.068).

TABLE 1

Demographics of Genetic Study Sample (N = 170)

|  | Patients | | Normals | |
| --- | --- | --- | --- | --- |
|  | n | % | n | % |
| Sample size | 124 | | 46 | |
| Mean age | 35.4 | | 38.3 | |
| Sex | | | | |
| Men | 83 | 66.9 | 28 | 60.9 |
| Women | 41 | 33.1 | 18 | 39.1 |
| Ethnicity | | | | |
| African-American | 46 | 37.1 | 16 | 34.8 |
| Caucasian | 58 | 46.8 | 23 | 50.0 |
| Hispanic | 20 | 16.1 | 6 | 13.0 |
| Asian | 0 | 0.0 | 1 | 2.2 |
| Diagnosis | | | | |
| Schizophrenia | 56 | 45.2 | | |
| Schizoaffective | 32 | 25.8 | | |
| Bipolar | 10 | 8.1 | | |
| Major Depressive | 10 | 8.1 | | |
| Other diagnoses | 16 | 12.9 | | |
| TD prevalence | 69 | 55.6 | | |

TABLE 2

Diagnosis by Ethnic Group in Patients

| Diagnosis | African-American | | Caucasian | | Hispanic | |
| --- | --- | --- | --- | --- | --- | --- |
|  | n | % | n | % | n | % |
| Schizophrenia | 24 | 52.2 | 20 | 34.5 | 12 | 60.0 |
| Schizoaffective | 11 | 23.9 | 17 | 29.3 | 4 | 20.0 |
| Bipolar | 5 | 10.9 | 5 | 8.6 | 0 | 0 |
| Major Depressive | 2 | 4.3 | 5 | 8.6 | 3 | 15.0 |
| Other | 4 | 8.7 | 11 | 19.0 | 1 | 5.0 |

Genomic DNA was isolated from blood samples and was analyzed by PCR amplification of 13 fragments covering the entire coding sequence and splice junctions of the PAH gene, followed by denaturing gradient gel electrophoresis (DGGE) according to the method of Guldberg et al. ("Mutational spectrum of phenylalanine hydroxylase deficiency in Sicily: implications for diagnosis of hyperphenylalaninemia in Southern Europe",*Human Molecular Genetics,* 1993, 2: 1703–1707) and for exon 10, as described by Guldberg P et al. ("Phenylalanine hydroxylase gene mutations in the United States; Report from the Maternal PKU Collaborative Study", *Am. J. Hum. Genet,* 1996, 59: 84–94).

The PCR amplification primer pairs (SEQ ID Nos. 1–26, Table 3) were designed using the OLIGO primer analysis program. To generate fragments suitable for analysis by DGGE, one of each primer pair included an additional GC-rich sequence (GC clamp) at its 5' end (with the position of the GC clamp determined using the MELT 87 computer algorithm). DGGE detects single base alterations on the basis that DNA fragments differing by a single base substitution will, by virtue of altered melting characteristics, migrate differently in a denaturing gel. The PCR-amplified DNA fragments were fractionated on 6% polyacrylamide gels with urea and formamide gradients. After electrophoresis, band patterns were visualized using a phosphorimager or BioDoc II Video Documentation System. Direct sequence analysis of samples was performed with the ABI Prism DNA sequencing system in cases where a more complex pattern was detected (Guldberg P and Guttler F, "A simple method for identification of point mutations using denaturing gradient gel electrophoresis", *Nucleic Acids Res.,* 1993, 21: 2261–2; Guldberg P et al., "Molecular analysis of phenylketonuria in Denmark: 99% of the mutations detected by denaturing gradient gel electrophoresis", *Genomics,* 1993, 17: 141–6; Guldberg P et al., "Phenylalanine hydroxylase gene mutations in the United States: report from the Maternal PKU Collaborative Study", *Am J Hum Genet.,* 1996, 59: 84–94).

TABLE 3

Amplification Primers and Denaturing Gradient Gel Electrophoresis (DGGE) Primer Conditions

| Sequence ID Number | Exon | Primer Sequence | Length of Amplified Segment (bp) | De-naturant range (%) | Electro-phoresis time (h) |
|---|---|---|---|---|---|
| 1 | 1 | 5' [GC]-TTAAAACCTTCAGCCCCACG 3' | 237 | 35–75 | 5 |
| 2 | | 5' TGGAGGCCCAAATTCCCCTAACTG 3' | | | |
| 3 | 2 | 5' GAGGTTTAACAGGAATGAATTGCT 3' | 304 | 15–55 | 6 |
| 4 | | 5' [GC]-TCCTGTGTTCTTTTCATTGC 3' | | | |
| 5 | 3 | 5' [GC]-GCCTGCGTTAGTTCCTGTGA 3' | 307 | 20–60 | 5 |
| 6 | | 5' CTTATGTTGCAAAATTCCTC 3' | | | |
| 7 | 4 | 5' ATGTTCTGCCAATCTGTACTCAGGA 3' | 199 | 30–70 | 6 |
| 8 | | 5' [GC]-CAAGACATAGGCCATGGACT 3' | | | |
| 9 | 5 | 5' TCATGGCTTTAGAGCCCCCA 3' | 253 | 20–60 | 5 |
| 10 | | 5' [GC]-AGGCTAGGGGTGTGTTTTC 3' | | | |
| 11 | 6 | 5' [GC]-CCGACTCCCTCTGCTAACCT 3' | 369 | 15–60 | 6 |
| 12 | | 5' CAATCCTCCCCCAACTTTCT 3' | | | |
| 13 | 7 | 5' [GC]-GGTGATGAGCTTTTAGTTTTCTTTC 3' | 303 | 25–65 | 6 |
| 14 | | 5' AGCAAATGAACCCAAACCTC 3' | | | |
| 15 | 8 | 5' [GC]-TGGCTTAAACCTCCTCCCCT 3' | 229 | 20–60 | 5 |
| 16 | | 5' CTGGGCTCAACTCATTTGAG 3' | | | |
| 17 | 9 | 5' ATGGCCAAGTACTAGGTTGG 3' | 225 | 20–60 | 6 |
| 18 | | 5' [GC]-GAGGGCCATAGACTATAGCA 3' | | | |
| 19 | 10 | 5' [GC]-TTAACGATCATAGAGTGTGC 3' | 214 | * | 4.5 |
| 20 | | 5' TTAAATCTATCCTTGGTTCCTGTG 3' | | | |
| 21 | 11 | 5' TGAGAGAAGGGGCACAAATG 3' | 341 | 15–60 | 6 |
| 22 | | 5' [GC]-GCCAACCACCCACAGATGAG 3' | | | |
| 23 | 12 | 5' ATGCCACTGAGAACTCTCTT 3' | 232 | 20–60 | 6 |
| 24 | | 5' [GC]-GATTACTGAGAAAGTGGCCT 3' | | | |
| 25 | 13 | 5' [GC]-GACACTTGAAGAGTTTTTGC 3' | 230 | 15–55 | 5 |
| 26 | | 5' TTTTCGGACTTTTTCTGATG 3' | | | |
| | | [GC] = CGCCCGCCGCGCCCCGCGCCCGTCCCGCCGCCCCGCCCG | | | |

*Guldberg, P. et al. "Phenylalanine hydroxylase gene mutations in the United States: report from the Maternal PKU Collaborative Study" *Am. J Hum. Genet.,* 1996; 59:84–94

The DNA analysis of the PAH gene in these subjects revealed ten polymorphisms and two mutations, designated as SEQ ID Nos. 27–38 (Table 4). Of these observed variants, four of the polymorhisms and one of the mutations (K274E) were novel. The novel variants are designated N133N (a T to C substitution in the final nucleotide of codon 133), L321L (a C to T substitution at the least nucleotide of codon 321), N426N (a T to C substitution at the final nucleotide of codon 426) and IVS6nt-7 (an A to T substitution at position-7 of intron 6). The novel K274E mutation (an AAG to GAG change in codon 274) results in a lysine to glutamic acid substitution at amino acid 274 in the PAH protein.

our subject population are putative 'silent' mutations (Phenylalanine hydroxylase locus database home page; 1998; http: www.mcgill.ca/pahdb/). The A403V mutation, which has been correlated with a mild hyperphenylalanemic phenotype (Guldberg P et al., "A European multicenter study of phenylalanine hydroxylase deficiency: classification of 105 mutations and a general system for genotype-based

TABLE 4

Sequences Surrounding PAH Variants Identified

| Sequence ID # | Variant Name | Base Change | Sequence* | Sequence ID #s of Primers for DGGE Detection |
|---|---|---|---|---|
| 27 | IVS2nt19 | t->c | 5' t a c a a t c a t g c t t g t c t t g g a 3' | 3, 4 |
| 28 | IVS3nt-22 | c->t | 5' g t a c t c a g g a t g t t g c c t t c t 3' | 7, 8 |
| 29 | IVS6nt-7 | a->t | 5' t c t t c t t t t c t t c c c a g CTTG 3' | 13, 14 |
| 30 | N133N | T->C | 5' GATTTGCCAACCAGATTCTCA 3' | 7, 8 |
| 31 | Q232Q | A->G | 5' ACGTTTCTCAGTTCCTGCAGA 3' | 11, 12 |
| 32 | V245V | G->A | 5' TCCGACCTGTAGCTGGCCTGC 3' | 13, 14 |
| 33 | L321L | C->T | 5' TTGAAAAGCTTGCCACA g t a a 3' | 17, 18 |
| 34 | L385L | G->C | 5' TCCAGCCCCTCTATTACGTGG 3' | 21, 22 |
| 35 | Y414Y | C->T | 5' CAGTTCGCTATGACCCATACA 3' | 23, 24 |
| 36 | N426N | T->C | 5' TCTTGGACAACACCCAGCAGC 3' | 23, 24 |
| 37 | K274E | A->G | 5' ACATGGATCCGAGCCCATGTA 3' | 13, 14 |
| 38 | A403V | C->T | 5' a g GAACTTTGTTGCCACAATA 3' | 23, 24 |

*Note:
intronic sequences are designated by lower-case letters and the polymorphic nucleotide is underlined.

Example 2

Frequency and Distribution of PAH Sequence Variants in Patients and Control Subjects A genetic screen of PAH in a population of 124 public sector psychiatric patients and 46 control subjects was conducted to investigate the hypothesis that psychiatric patients have PAH mutations which could have long term effects including predisposition to psychiatric disorders. A total of ten polymorphisms and two mutations were found on the PAH gene in our subject population, of which four of the polymorphisms and one of the mutations were novel. The frequency and distribution of PAH variants in the patient population and in the control population have been partitioned by ethnic group in Tables 5 and 6 respectively. The previously described IVS2nt19, IVS3nt-22, Q232Q, V245V, L385L and Y414Y variants that were observed in prediction of metabolic phenotype, *Am J Hum Genet*, 1998, 63: 71–79; Desviat L R et al., "Molecular basis of non-PKU hyperphenylalaninaemia in Spain: prevalence of A403V, a mutation with high residual activity", *J Inherit Metab Dis*, 1996, 19: 227–230; Zekanowski C et al., "Molecular basis of mild hyperphenylalaninaemia in Poland", *J Med Genet*, 1997, 34: 1035–1036) was observed in our study in one Caucasian patient with schizophrenia. The novel K274E missense mutation was identified in four African-American schizophrenic patients and in one control subject, and none of these individuals was homozygous for the mutation. The African-American control subject who was heterozygous for the K274E mutation was homozygous for the L321L polymorphism. All patients heterozygous for the K274E mutation were also heterozygous for the L321L polymorphism, and there was a statistically significant association between these two PAH variants (Fisher's Exact Test, $p<0.001$).

TABLE 5

Frequency and Distribution of PAH Sequence Variants in Patients

| Sequence Variation | African-American 92 Alleles | Caucasian 116 Alleles | Hispanic 40 Alleles |
|---|---|---|---|
| IVS2nt19 T/C | T: 0.82 C: 0.18 | T: 0.87 C: 0.13 | T: 0.72 C: 0.27 |
| IVS3nt-22 C/T | C: 0.92 T: 0.08 | C: 0.77 T: 0.23 | C: 0.80 T: 0.20 |

TABLE 5-continued

Frequency and Distribution of PAH Sequence Variants in Patients

| Sequence Variation | | African-American 92 Alleles | Caucasian 116 Alleles | Hispanic 40 Alleles |
|---|---|---|---|---|
| IVS6nt-7* | A/T | A: 0.95 T: 0.05 | A: 0.98 T: 0.02 | A: 0.97 T: 0.03 |
| N133N* | AAT/AAC | NP: T | T: 0.99 C: 0.01 | NP: T |
| Q232Q | CAA/CAG | A: 0.80 G: 0.20 | A: 0.58 G: 0.42 | A: 0.70 G: 0.30 |
| V245V | GTG/GTA | G: 0.98 A: 0.02 | G: 0.73 A: 0.27 | G: 0.82 A: 0.18 |
| L321L* | CTC/CTT | C: 0.92 T: 0.08 | NP: C | NP: C |
| L385L | CTG/CTC | G: 0.79 C: 0.21 | G: 0.85 C: 0.15 | G: 0.90 C: 0.10 |
| Y414Y | TAC/TAT | NP: C | C: 0.99 T: 0.01 | NP: C |
| N426N* | AAT/AAC | T: 0.79 C: 0.21 | NP: T | T: 0.95 C: 0.05 |
| K274E* | AAG/GAG | A: 0.96 G: 0.04 | NP: A | NP A |
| A403V | GCT/GTT | NP: C | C: 0.99 T: 0.01 | NP C |

*novel sequence variants, NP = no polymorphism
Frequencies for each group were calculated by dividing the number of occurrences of a particular variant by the total number of alleles in the group

TABLE 6

Frequency and Distribution of PAH Sequence Variants in Normal Subjects

| Sequence Variation | | African-American 32 Alleles | Caucasian 46 Alleles | Hispanic 12 Alleles | Asian 2 Alleles |
|---|---|---|---|---|---|
| IVS2nt19 | T/C | T: 0.84 C: 0.16 | T: 0.78 C: 0.22 | T: 0.83 C: 0.17 | NP: T |
| IVS3nt-22 | C/T | C: 0.84 T: 0.16 | C: 0.89 T: 0.11 | C: 0.67 T: 0.33 | C: 0.50 T: 0.50 |
| IVS6nt-7* | A/T | A: 0.97 T: 0.03 | NP: A | NP: A | NP: A |
| N133N* | AAT/AAC | NP: T | NP: T | NP: T | NP: T |
| Q232Q | CAA/CAG | A: 0.66 G: 0.34 | A: 0.63 G. 0.37 | A: 0.42 G: 0.58 | A: 0.50 G: 0.50 |
| V245V | GTG/GTA | G: 0.91 A: 0.09 | G: 0.85 A: 0.15 | G: 0.58 A: 0.42 | G: 0.50 A: 0.50 |
| L321L* | CTC/CTT | C: 0.84 T: 0.16 | NP: C | NP: C | NP: C |
| L385L | CTG/CTC | G: 0.75 C: 0.25 | G: 0.80 C: 0.20 | G: 0.75 C: 0.25 | NP: G |
| Y414Y | TAC/TAT | NP: C | C: 0.96 T: 0.04 | NP: C | NP: C |
| N426N* | AAT/AAC | T: 0.81 C: 0.19 | NP: T | T: 0.92 C: 0.08 | NP: T |
| K274E* | AAG/GAG | A: 0.97 G: 0.03 | NP: A | NP: A | NP: A |
| A403V | GCT/GTT | NP: C | NP: C | NP: C | NP: C |

*novel sequence variants, NP = no polymorphism
Frequencies for each group were calculated by dividing the number of occurrences of a particular variant by the total number of alleles in the group Example 3

The Association of PAH Genetic Polymorphisms with Schizophrenia and Ethnic Status A genetic screen of PAH in a population of 124 public sector psychiatric patients and 46 control subjects was conducted to investigate the hypothesis that psychiatric patients have PAH mutations which could have long term effects including predisposition to psychiatric disorders. The genetic analysis of the PAH locus in psychiatric patients enabled an evaluation of statistical associations of PAH polymorphisms with the diagnosis of schizophrenia (Table 7). The L321L polymorphism had a positive association with schizophrenia and the IVS2nt19 polymorphism showed a similar trend. The A403V mutation was observed in one Caucasian patient in this study, and this subject was diagnosed as schizophrenic. The novel K274E mutation was shown by statistical analysis to be positively associated with a diagnosis of schizophrenia in this patient population.

The novel variants L321L and N426N, as well as the novel mutation K274E, showed a significant association with African-American ethnicity. The variants IVS3nt-22, Q232Q, and V245V showed a significant association with Caucasian ethnicity, and the one schizophrenic patient with the A403V mutation was Caucasian.

No positive associations were seen for TD with any of the variants (data not shown).

frequency were observed between subjects of African and European descent (Cloninger C R et al., "Genome-wide search for schizophrenia susceptibility loci: the NIMH Genetics Initiative and Millenium Consortium:, *Am J Med Genet,* 1998, 81:275–281) and there is precedent for ethnic differences with regard to the genetic basis of disease susceptibility (Tang M X et al., "The APOE-epsilon4 allele

TABLE 7

Association Between PAH Variants and Schizophrenia, African-American Ethnicity, and Caucasian Ethnicity in Patients (n = 124)

| Variant | | Schizophrenia | | | African American | | | Caucasian | | |
|---|---|---|---|---|---|---|---|---|---|---|
| | | Yes | No | Prob[1] | Yes | No | Prob[1] | Yes | No | Prob[1] |
| IVS2nt19 | Yes | 22 (56%) | 17 (44%) | .066 | 16 (41%) | 23 (59%) | ns | 14 (36%) | 25 (64%) | ns |
| | No | 34 (40%) | 51 (60%) | | 30 (35%) | 55 (65%) | | 44 (52%) | 41 (48%) | |
| LVS3nt-22 | Yes | 15 (39%) | 23 (61%) | ns | 7 (18%) | 31 (82%) | ns | 24 (63%) | 14 (37%) | .013 |
| | No | 41 (48%) | 45 (52%) | | 39 (45%) | 47 (55%) | | 34 (40%) | 52 (60%) | |
| IVS6nt-7* | Yes | 4 (50%) | 4 (50%) | ns | 5 (62%) | 3 (38%) | ns | 2 (25%) | 6 (75%) | ns |
| | No | 52 (45%) | 64 (55%) | | 41 (35%) | 75 (65%) | | 56 (48%) | 60 (52%) | |
| N133N* | Yes | 0 (0%) | 1 (100%) | ns | 0 (0%) | 1 (100%) | ns | 1 (100%) | 0 (0%) | ns |
| | No | 56 (46%) | 67 (54%) | | 46 (37%) | 77 (63%) | | 57 (46%) | 66 (54%) | |
| Q232Q | Yes | 28 (43%) | 37 (57%) | ns | 16 (25%) | 49 (75%) | ns | 41 (63%) | 24 (37%) | <.001 |
| | No | 28 (47%) | 31 (53%) | | 30 (51%) | 29 (49%) | | 17 (29%) | 42 (71%) | |
| V245V | Yes | 11 (31%) | 25 (69%) | ns | 2 (6%) | 34 (94%) | ns | 28 (78%) | 8 (22%) | <.001 |
| | No | 45 (51%) | 43 (49%) | | 44 (50%) | 44 (50%) | | 30 (34%) | 58 (66%) | |
| L321L* | Yes | 6 (86%) | 1 (14%) | .032 | 7 (100%) | 0 (0%) | <.001 | 0 (0%) | 7 (100%) | ns |
| | No | 50 (43%) | 67 (57%) | | 39 (33%) | 78 (67%) | | 58 (50%) | 59 (50%) | |
| L385L | Yes | 19 (53%) | 17 (47%) | ns | 17 (47%) | 19 (53%) | .099 | 15 (42%) | 21 (58%) | ns |
| | No | 37 (42%) | 51 (58%) | | 29 (33%) | 59 (67%) | | 43 (49%) | 45 (51%) | |
| Y414Y | Yes | 1 (100%) | 0 (0%) | ns | 0 (0%) | 1 (100%) | ns | 1 (100%) | 0 (0%) | ns |
| | No | 55 (45%) | 68 (55%) | | 46 (37%) | 77 (63%) | | 57 (46%) | 66 (54%) | |
| N426N* | Yes | 9 (47%) | 10 (53%) | ns | 17 (89%) | 2 (11%) | <.001 | 0 (0%) | 19 (100%) | ns |
| | No | 47 (45%) | 58 (55%) | | 29 (28%) | 76 (72%) | | 58 (55%) | 47 (45%) | |
| K274E* | Yes | 4 (100%) | 0 (0%) | .039 | 4 (100%) | 0 (0%) | .017 | 0 (0%) | 4 (100%) | ns |
| | No | 52 (43%) | 68 (57%) | | 42 (35%) | 78 (65%) | | 58 (48%) | 62 (52%) | |
| A403V | Yes | 1 (100%) | 0 (0%) | ns | 0 (0%) | 1 (100%) | ns | 1 (100%) | 0 (0%) | ns |
| | No | 55 (45%) | 68 (55%) | | 46 (37%) | 77 (63%) | | 57 (46%) | 66 (54%) | |

[1]Probability value from Fisher Exact Test (one-tailed); 'ns' indicates p > 0.10; *novel polymorphic sites Thus for the PAH variants that have been identified in the sample of psychiatric patients, statistically significant associations of specific polymorphisms with a diagnosis of schizophrenia and/or with ethnicity was detected, as summarized in Table 8. Since in a genomic screen for schizophrenia loci, differences in genetic heterozygosity and allele and the risk of Alzheimer disease among African Americans, whites, and Hispanics" JAMA, 1998, 279: 751–755), the ethnic homogeneity observed for the schizophrenia-associated K274E and L321L variants increases their likely usefulness in identifying genetic components of the complex disorder of schizophrenia.

TABLE 8

Summary of PAH Variant Characteristics

| Variant (Base Change) | Location | Comment |
|---|---|---|
| IVS2nt19 (T->C) | intron 2 splice junction | Known polymorphism; statistical trend for association with schizophrenic status (p = .066) |
| IVS3nt-22 (C->T) | intron 3 splice junction | Known polymorphism; significant association with Caucasian status |
| IVS6nt-7 (A->T) | intron 6 splice junction | Novel polymorphism; all schizophrenics with this variant are African-American |
| N133N (AAT->AAC) | amino acid 133 regulatory domain | Novel polymorphism |
| Q232Q (CAA->CAG) | amino acid 232 catalytic domain | Known polymorphism; significant association with Caucasian status |
| V245V (GTG->GTA) | amino acid 245 catalytic domain | Known polymorphism; significant association with Caucasian status |
| L321L (CTC->CTT) | amino acid 321 catalytic domain | Novel polymorphism; significant association with schizophrenic and African-American status |
| L385L (CTG->CTC) | amino acid 385 catalytic domain | Known polymorphism; statistical trend for association with African-American status |

TABLE 8-continued

Summary of PAH Variant Characteristics

| Variant (Base Change) | Location | Comment |
|---|---|---|
| Y414Y (TAC->TAT) | amino acid 414 intersubunit binding region | Known polymorphism |
| N426N (AAT->AAC) | amino acid 426 intersubunit binding region | Novel polymorphism; significant association with African-American status; 7 of the 9 schizophrenics with this variant were African-American |
| K274E (AAG->GAG) | amino acid 274 catalytic domain $BH_4$ binding site | Novel missense mutation; significant association with schizophrenic and African-American status |
| A403V (GCT->GTT) | amino acid 403 catalytic domain | Known mutation considered to be hyperphenylalanemic; seen in one person with schizophrenia who demonstrated the most difficulty in our sample of 124 patients in Phe metabolism (conversion to tyrosine) |

Example 4

Plasma Measures Related to the Presence of Novel PAH Variants

A genetic screen of PAH in a population of 124 public sector psychiatric patients and 46 control subjects was conducted to investigate the hypothesis that psychiatric patients have PAH mutations which could have long term effects including predisposition to psychiatric disorders. In order to investigate the possible functional consequences of PAH variants in vivo, plasma measures of biopterins, neopterins, phenylalanine (Phe), and tyrosine were assessed. For each patient, a blood sample was drawn in the morning following a fasting period of $\geq 8.5$ hours, and a second blood sample was drawn two hours after the administration of an oral Phe dose (100 mg Phe per kg of body weight, in 170 ml orange juice).

Plasma biopterin and neopterin values were determined by high performance liquid chromatography using an ion-paired reverse phase system and fluorometric detection (Fukushima T et al., "Analysis of reduced forms of biopterin in biological tissues and fluids", *Analytical Biochemistry,* 102:176–188, 1980; Lunte C E and Kissinger P T, "Determination of pterins in biological samples by liquid chromatography/electrochemistry with a dual-electrode detector", *Analytical Chemistry,* 55:1458–1462, 1983). The measurement for total biopterins includes the tetrahydrobiopterin ($BH_4$), dihydrobiopterin and biopterin forms, and about 90% of the total is in the form of $BH_4$. The measurement for total neopterins includes the dihydroneopterin and neopterin forms (Levine, R. A. "Tetrahydrobiopterin and biogenic amine metabolism in neuropsychiatry, immunology, and aging" *Annals of the New York Academy of Sciences* 1988; 521: 129–139., Kay, A. D. et al., "Cerebrospinal fluid biopterin is decreased in Alzheimer's disease" *Arch. Neurol.* 1986; 43: 996–999.).

Plasma phenylalanine and tyrosine were analyzed by a modified procedure (Hariharan M et al., "Systematic approach to the development of plasma amino acid analysis by high-performance liquid chromatography with ultraviolet detection with precolumn derivatization using phenyl isothiocyanate", *J Chromatogr,* 1993, 621: 15–22) using phenylisothiocyanate (PITC) derivatization followed by HPLC. The internal standard norleucine was added to 0.25 ml of plasma sample. The supernatant from the plasma following deproteinization with 0.5 ml acetonitrile and centrifugation, was extracted with 2 ml methyl-t-butyl ether, and centrifuged. Following aspiration of the ether, the aqueous portion was dried under vacuum. The residue, redissolved in 40$\mu$l of ethanol: triethylamine: water (2:1:2), was redried. 50 $\mu$l ethanol: triethylanine: water: PITC (7:1:1:1) was added, and after 20 minutes at room temperature, removed under vacuum. Before chromatography, the residues were redissolved in phosphate buffer/5% acetonitrile. Standards of free amino acids in 5% bovine albumin were processed in parallel. HPLC was performed using a solvent delivery system consisting of two Model 590 pumps and a Model 486 variable wavelength UV detector (254 nm). The solvent gradient was controlled with a Model 680 gradient programmer and the samples injected by a Model 717 WISP autoinjector (all equipment by Waters Assoc.). The dual solvent system was aqueous 0.14M sodium acetate containing 0.8 ml/L of triethylamine, titrated to pH 6.8 with glacial acetic acid in 4% acetonitrile (A), and 60% acetonitrile in water (B). The gradient traversed from 2% B to 46% B (flow rate 1.0 ml/min) for 15 minutes following convex curve #5 on the Model 680 Gradient Programmer. Prior to re-equilibration, 90% B was flushed through the reversed-phase Nova-Pak C18 column (3.9×300 mm, controlled at 40° C.). Sample peak heights were compared to peak heights of amino acid standards processed simultaneously (using norleucine as the internal standard) and a calibration curve developed from the standards was used to quantitate each amino acid.

The results showed that patients with the K274E mutation had a significantly higher level of fasting tyrosine, a statistically significant lower level of both total neopterin and a lower neopterin/biopterin ratio, as well as a statistical trend for a higher level of total biopterin, than patients without the mutation. After the Phe dose, plasma Phe levels were significantly higher in patients with the mutation, suggesting a slower clearance of the ingested Phe. In patients with the mutation, the percent change from fasting to post-Phe dose in amino acid levels was significantly higher for the change in Phe and significantly lower for the change in tyrosine, than in patients without the mutation, suggesting a reduced conversion to tyrosine.

TABLE 9

Plasma Measures in Patients with and without the K274E Mutation

| Plasma Variable | With K274E Mutation n = 4 (Median) | No K274E Mutation n = 120 (Median) | z | Prob[1] |
|---|---|---|---|---|
| Fasting Values: | | | | |
| Total Neopterin (nmol/ml) | 0.0034 | 0.0053 | −2.77 | .006 |
| Total Biopterin (nmol/ml) | 0.0154 | 0.0106 | 1.70 | .090 |
| Neopterin/Biopterin Ratio | 0.2228 | 0.5200 | −3.09 | .002 |
| Phenylalanine (nmol/ml) | 59.5 | 57.0 | 1.06 | ns |
| Tyrosine (nmol/ml) | 102.5 | 65.5 | 2.98 | .003 |
| Post Phe Dose Values: | | | | |
| Phenylalanine (nmol/ml) | 703.5 | 433.0 | 2.52 | .012 |
| Tyrosine (nmol/ml) | 172.0 | 140.0 | 0.87 | ns |
| Percent Change from Fasting to Post Phe Dose[2]: | | | | |
| Phenylalanine | 956.01 | 633.45 | 2.24 | .025 |
| Tyrosine | 54.92 | 109.43 | −2.19 | .029 |

[1]Probability value from Wilcoxon 2-Sample Test; "ns" indicates $p > 0.10$
[2]Percent change = ((post Phe dose − fasting) / fasting) * 100

These data demonstrate that in patients with the K274E mutant PAH protein, there is a reduced ability to convert the ingested Phe to tyrosine. The significant differences in neopterin and the neopterin/biopterin ratio, indicate an increase in $BH_4$ synthesis in those with the mutation. Increases in biopterin levels have been observed in patients with PKU and have been interpreted as a compensatory mechanism for deficits in PAH activity (Guttler F et al., Combined tetrahydrobiopterin-phenylalanine loading test in the detection of partially defective biopterin synthesis", *Eur J Pediatr*, 1984, 142:126). These attendant changes in amino acid and pterin homeostasis provide physiological evidence for the functional significance of the novel K274E mutation.

Significant changes in plasma amino acids and pterins were associated with another novel PAH variant, namely the L321L polymorphism (Table 10). The differences accompanying the L321L variant were similar to those for the K274E mutation, namely that in patients with L321L there was a significantly higher fasting level of tyrosine, higher post-Phe intake level of plasma Phe, lesser change in tyrosine from fasting to post-Phe dose and a statistical trend for a higher level of fasting biopterin, than in those without the L321L variant. Although the L321L polymorphism is not predicted to affect the PAH protein sequence, it is of interest to note that alterations in Phe metabolism (perhaps indicative of changes in PAH function) are associated with the presence of this genetic variant.

TABLE 10

Plasma Measures in Patients with and without the L321L Polymorphism

| Plasma Variable | With L321L Polymorphism n = 7 (Median) | No L321L Polymorphism n = 117 (Median) | z | Prob[1] |
|---|---|---|---|---|
| Fasting Values: | | | | |
| Total Neopterin (nmol/ml) | .0038 | .0053 | −.857 | ns |
| Total Biopterin (nmol/ml) | .0152 | .0106 | 1.894 | .058 |
| Neopterin/Biopterin Ratio | .3368 | .5198 | −1.13 | ns |
| Phenylalanine (nmol/ml) | 60.0 | 57.0 | 1.547 | ns |
| Tyrosine (nmol/ml) | 100.0 | 65.0 | 2.898 | .004 |
| Post Phe Dose Values: | | | | |
| Phenylalanine (nmol/ml) | 568.0 | 429.0 | 2.069 | .039 |
| Tyrosine (nmol/ml) | 173.0 | 139.5 | 1.518 | ns |
| Percent Change from Fasting to Post Phe Dose[2]: | | | | |
| Phenylalanine | 758.33 | 636.00 | 1.431 | ns |
| Tyrosine | 55.556 | 110.10 | −2.03 | .043 |

[1]Probability value from Wilcoxon 2-Sample Test; "ns" indicates $p > 0.10$
[2]Percent change = ((post Phe dose − fasting) / fasting) * 100

The significant association between the K274E and L321L variants in our patient group, the biochemical profiles observed in patients with these variants, and the statistical association of both variants to African-American ethnicity and the diagnosis of schizophrenia, suggest that these novel PAH variants may be useful as genetic markers of a particular etiological/pathological subtype of schizophrenia and susceptibility to schizophrenia in African-Americans.

Example 5

Plasma Measures Related to the Presence of Previously Described PAH Variants

Plasma analysis performed as described above in Example 4, supported the predicted hyperphenylalanemic state of the A403V mutation, which we identified in one Caucasian schizophrenic patient. Descriptive differences between plasma values for the A403V patient and the mean for the group of all patients are most apparent subsequent to the Phe dose (Table 11). This patient had the lowest change, among the patients, in tyro sine from fasting to post-Phe dose, and among the highest change in Phe from fasting to post-Phe intake. These data suggest that a reduced conversion of the Phe intake to tyrosine occurred in this schizophrenic patient as would be expected for a person with hyperphenylalanemia.

TABLE 11

Plasma Measures and Ranks in Patient with the A403V Mutation

| | Patient with A403V Mutation | | All Patients (n = 124) | |
|---|---|---|---|---|
| Plasma Variable | Value | Rank | Mean | SD |
| Fasting Values: | | | | |
| Total Neopterin (nmol/ml) | 0.0077 | 99 | 0.0063 | 0.0038 |
| Total Biopterin (nmol/ml) | 0.0111 | 72 | 0.0115 | 0.0044 |
| Neopterin/Biopterin Ratio | 0.6937 | 108 | 0.5970 | 0.5151 |
| Phenylalanine (nmol/ml) | 71.0 | 115 | 57.8 | 7.8 |
| Tyrosine (nmol/ml) | 92.0 | 113 | 69.2 | 16.1 |
| Post Phe Dose Values: | | | | |
| Phenylalanine (nmol/ml) | 937.0 | 123 | 452.5 | 152.8 |
| Tyrosine (nmol/ml) | 98.0 | 8 | 147.8 | 42.1 |
| Percent Change from Fasting to Post Phe Dose: | | | | |
| Phenylalanine | 1219.7 | 119 | 690.0 | 267.6 |
| Tyrosine | 6.5 | 1 | 118.8 | 66.0 |

Percent change = ((post Phe dose − fasting) / fasting) * 100

For the IVS2nt19 polymorphism a different profile of Phe association was apparent (one suggestive of dysregulation)

with lower plasma Phe levels following Phe intake and a lesser change in plasma Phe from fasting to post-Phe dose associated with the presence of the IVS2nt19 variant (Table 12).

TABLE 12

Plasma Measures in Patients with and without the IVS2nt19 Polymorphism

| Plasma Variable | With IVS2nt19 Polymorphism n = 39 (Median) | No IVS2nt19 Polymorphism n = 85 (Median) | z | Prob[1] |
|---|---|---|---|---|
| Fasting Values: | | | | |
| Total Neopterin (nmol/ml) | .0051 | .0055 | −.772 | ns |
| Total Biopterin (nmol/ml) | .0105 | .0107 | .4571 | ns |
| Neopterin/Biopterin Ratio | .5198 | .5198 | −.379 | ns |
| Phenylalanine (nmol/ml) | 58.0 | 56.0 | .2713 | ns |
| Tyrosine (nmol/ml) | 67.0 | 65.0 | .7107 | ns |
| Post Phe Dose Values: | | | | |
| Phenylalanine (nmol/ml) | 407.0 | 451.5 | −2.33 | .020 |
| Tyrosine (nmol/ml) | 145.0 | 136.5 | 1.283 | ns |
| Percent Change from Fasting to Post Phe Dose[2]: | | | | |
| Phenylalanine | 606.43 | 693.73 | −2.38 | .017 |
| Tyrosine | 111.32 | 102.98 | .9403 | ns |

[1]Probability value from Wilcoxon 2-Sample Test; "ns" indicates p > 0.10
[2]Percent change = ((post Phe dose − fasting) / fasting) * 100

These plasma measures of pterins and amino acids (fasting and post-Phe dose) serve as a means of characterizing the functional correlates of specific PAH polymorphisms and substantiate previous findings that different PAH variants can have markedly different phenotypic and physiological associations (Waters P J et al., "In vitro expression analysis of mutations in phenylalanine hydroxylase: linking genotype to phenotype and structure to function", *Hum Mutat*, 1998, 11:4–17; Guldberg P et al., "A European multicenter study of phenylalanine hydroxylase deficiency: classification of 105 mutations and a general system for genotype-based prediction of metabolic phenotype", *Am J Hum Genet*, 1998, 63: 71–79).

Example 6

Changes in the Chemical, Structural and Regulatory Properties of the PAH Protein are Predicted for the K274E Mutation The site of the novel K274E mutation lies within the catalytic domain of the PAH protein, in a region that is highly conserved among aromatic amino acid hydroxylases and is considered to be involved in binding the enzyme cofactor tetrahydrobiopterin ($BH_4$) (Hufton S E et al., "Structure and function of the aromatic amino acid hydroxylases", *Biochem. J.*, 1995, 311: 353–366; Waters P J et al., "In vitro expression analysis of mutations in phenylalanine hydroxylase: linking genotype to phenotype and structure to function", *Hum. Mutat.*, 1998, 11:4–17; Dickson P W et al., "Delineation of the catalytic core of phenylalanine hydroxylase and identification of glutamate 286 as a critical residue for pterin function", *J. Biol. Chem.*, 1994, 269: 20369–20375; Jennings I G et al., "Localization of cofactor binding sites with monoclonal anti-idiotype antibodies: phenylalanine hydroxylase", *Proc. Natl.Acad. Sci.USA*, 1991, 88: 5734–5738). Computer modeling of the wild-type and mutated forms of the protein using the Protean program (DNAStar Inc., Lasergene molecular modeling program suite) predicts that a lysine to glutamic acid substitution at position 274 would shift the isoelectric point from 6.41 for the native enzyme, to 6.18 for the K274E mutant protein. The computer modeling suite also predicts that the K274E mutation would eliminate an area of Beta sheet structure (275–278) and create an area of Alpha amphipathic structure (246–249) which is not present in the native protein (Gill S C and von Hippel P H, "Calculation of protein extinction coefficients from amino acid sequence data", *Anal. Biochem.*, 1989, 182: 319–326; Garnier J et al., "Analysis of the accuracy and implications of simple methods for predicting the secondary structure of globular proteins", *J. Mol. Biol.*, 1978, 120: 97–120; Eisenberg D et al., "The hydrophobic moment detects periodicity in protein hydrophobicity", *Proc. Natl. Acad. Sci.USA*, 1984, 81: 140–144).

The crystal structure of PAH is not currently available. However, the Swiss-Model Protein program can be used to superimpose residues 150–452 of the human PAH enzyme onto the crystal structure of the highly homologous rat tyrosine hydroxylase (Abola E E et al., "Protein Data Bank archives of three-dimensional macromolecular structures", *Methods Enzymol.*, 1997, 277: 556–571; Guex N and Peitsch M C, "SWISS-MODEL and the Swiss-PdbViewer: an environment for comparative protein modeling", *Electrophoresis*, 1997, 18: 2714–□12723; personal communication from Gjetting T and Nielsen R). The resulting structural model for PAH places lysine 274 in a turn with the lysine residue pointing out towards the solvent, suggesting that it may not have direct interactions with other residues in the catalytic domain. However, since the N-terminal regulatory domain of PAH is likely to be in close proximity, the lysine 274 residue may participate in a salt bridge to a negative charge on the regulatory domain, an interaction that could be relevant to the conformational change that occurs upon activation of the enzyme. Speculatively, a glutamic acid in this position could participate in an illegitimate salt bridge to the regulatory domain, thereby disrupting the normal function of the enzyme (Fusetti F et al., "Structure of tetrameric human phenylalanine hydroxylase and its implications for phenylketonuria", *J. Biol. Chem.*, 1998, 273: 16962–16967; personal communication from Gjetting T and Nielsen R). Similar computer modeling using the crystal structure of the human PAH protein (Bjorgo E et al., "Partial characterization and three-dimensional structural localization of eight mutations in exon 7 of the human phenylalanine hydroxylase gene associated with phenylketonuria", *Eur J Biochem*, 1998,257:1–10) will give further insight into the potential physico-chemical and functional consequences of this novel PAH mutation. Further computer modeling of the effect of the novel K274E mutation will be performed when the crystal structure of human PAH becomes available.

Example 7

Studies to Determine the Functional Consequences of the Novel PAH Variants

The novel K274E mutation, which results in a a lysine to glutamic acid substitution at amino acid 274 in the PAH protein, has been investigated by computer modeling (see Example 6). In addition, in vitro expression analysis of the K274E mutation in eukaryotic, prokaryotic, and/or cell-free systems can be performed to ascertain the effect of this mutation on levels of PAH protein and enzymatic activity (Waters P J et al., "In vitro expression analysis of mutations in phenylalanine hydroxylase: linking genotype to phenotype and structure to function", *Hum Mutat*, 1998, 11:4–17).

While no changes in amino acid sequence can be ascribed to the novel PAH polymorphisms IVS6nt-7, N133N, L321L and N426N, it remains to be determined whether these variants affect PAH expression through other mechanisms. These putative other mechanisms (which could be examined using previously described in vitro assays) may include, but are not restricted to, changes in: a) splicing, e.g. by creating a cryptic splice site (Dworniczak B et al., "Aberrant splicing of phenylalanine hydroxylase mRNA: the major cause for phenylketonuria in parts of southern Europe", *Genomics*, 1991, 11:242–6), b) mRNA stability (Andreou E R and Prokipcak R D, "Analysis of human CYP7A1 mRNA decay in HepG2 cells by reverse transcription-polymerase chain reaction", *Arch Biochem Biophys*, 1998, 357:137–46), c) mRNA utilization e.g. by altering the mRNA secondary structure (Merrick W C and Sonenberg N, "Assays for eukaryotic translation factors that bind mRNA", *Methods*, 1997, 11:333–42) and d) methylation in the case of the L321L polymorphism, in which a CG dinucleotide is eliminated and a Hind III restriction enzyme site is created (Rein T et al., "Identifying 5-methylcytosine and related modifications in DNA genomes", *Nucleic Acids Res*, 1998, 26:2255).

Transgenic mice, carrying one or a combination of PAH variants, can be used to explore the in vivo consequences of the genetic polymorphisms on basal amino acid and pterin metabolism, as well as on brain availability of precursor amino acids and consequent neurotransmitter function following amino acid intake (Picciotto M R and Wickman K, "Using knockout and transgenic mice to study neurophysiology and behavior", *Physiol Rev*, 1998, 78: 1131–63).

Example 8

The Use of the PAH Variants as a Tool for the Definition of a Specific Etiology and Pathophysiology, and for the Identification of Susceptibility to the Development of the Disorder The best mode of practicing the invention will be demonstrated by using the example of the novel missense K274E mutation which we discovered on the PAH gene. The K274E mutation shows a statistical association with the psychotic disorder of schizophrenia in persons who are of African-American ethnicity. This association suggests that the mutation may be related to the pathophysiology and susceptibility to develop the Disorder of Schizophrenia in that ethnic group.

The presence of K274E mutation may be identified in two categories of persons with African ethnicity, as follows:

1. Adult persons of African ethnicity with schizophrenia. The majority of the persons with this disorder are in continual care in the public sector, either in state, Veterans Administration, county, or city hospitals, community residences, day programs, shelters, and living in the community (either singly or in families) but receiving outpatient care; and
2. Newborn, child, adolescent, or adult persons at risk of schizophrenia (first and second degree relatives of persons of African ethnicity with schizophrenia). These persons are best identified through their schizophrenic relatives who come in for treatment in either public sector or private facilities.

For the detection of this mutation, a blood sample of 1 ml or less or a buccal swab (or other tissue sample) will be collected from all persons to be screened. Screening for the mutation will be accomplished by the use of a test kit designed to allow for simple detection in any clinical genetic laboratory. This test kit will make use of the denaturing gradient gel electrophoresis (DGGE) methodology (including primers) that was successfully used in the discovery of this mutation and is elaborated in the Detailed Description of the Invention and Example 1.

The presence of the K274E mutation in persons of African ethnicity with schizophrenia could indicate the presence of a subtype of this psychotic disorder, a subtype that would be defined by a deficient metabolism of Phe and increased $BH_4$ synthesis (a homeostatic response to deficient Phe metabolism). This subtype could define the etiology, development and pathophysiology of the disorder in these persons. A developmental model for the susceptibility to schizophrenia for these persons, could be as follows:

(1) those with the mutation responded to dietary challenges of Phe with higher levels of plasma Phe and reduced conversion to tyrosine than those without the mutation, (2) the challenge experience of the DNA study may mimic real life in that those with the mutation experience higher levels of plasma Phe in response to their normal dietary intake (e.g. protein sources, aspartame), (3) these chronically higher levels of plasma Phe lead to a chronically reduced dopamine, noradrenaline and serotonin neurochemical substrate, (4) this neurochemical substrate can contribute to the development of "supersensitivities" to dopamine, noradrenaline and serotonin that may increase the vulnerability to the development of schizophrenia.

(5) treatment for schizophrenia in the persons with this subtype could be by the reduction of brain Phe levels (such treatment will be presented in Example 9.).

The linkage of the PAH variants with psychotic, mood and personality disorders in families may be established by analyzing family pedigrees for the presence K274E mutation or the other polymorphisms of the PAH gene described in Table 5 above. The Inventor has applied for and received permission to access the DNA samples collected by the National Institute of Mental Health Genetics Initiative (Cloninger C R et al., "Genome-wide search for schizophrenia susceptibility loci: The NIMH Genetics Initiative and Millennium Consortium", *Am J. Med Genet*, 1998, 81:275–281), the samples of which are obtained from families in which the proband and at least one living first-degree relative had the core phenotype diagnosis of schizophrenia or the depressed subtype of schizoaffective disorder.

The PAH variants of the present invention and found in schizophrenia are associated with ethnicity, therefore, the initial use of the database by the Inventor will be limited to pedigrees containing members identified as African-American, and a screening of the PAH variants identified in Example 1. Currently in the NIMH database this group consists of 35 pedigrees containing 175 family members that would be genotyped. Psychiatric diagnoses in these families include the following; 92 with Schizophrenia, 11 with Schizoaffective Disorder-Depressed type, 17 with Personality Disorders, and 14 with Mood Disorders. It is anticipated that more families will be added periodically to this database.

The denaturing gradient gel electrophoresis (DGGE) method was used in the original discovery of the PAH variants. However, due to speed and lower cost, the single stranded conformation polymorphism method (SSCP) may be used instead, to detect PAH variants. This method has gained the widest application in recent years and has become the preferred practice for detection of known gene sequence variants at the single base-pair level in a clinical laboratory environment (Orita-M et.al, "Detection of polymorphisms of human DNA by gel electrophoresis as single-stranded conformation polymorphisms", *Proc Natl Acad Sci USA,* 1989, 86: 2766–2760). PCR primers flanking each of the PAH variants (SEQ I.D.'s 39–62) are shown in Table 13 below. This technique relies on the property of single-stranded DNA to form specific semistable configurations be detected as an abnormal migratory band on the gel following autoradiography. The precise conditions of electrophoresis, such as temperature, gel percentage, and the addition of neutral compounds (such as glycerol and urea), also affect the mobility and ease of detecting mutations. However by using the PCR products from control individuals who are homozygous and heterozygous for each PAH variant under investigation, the optimum conditions of detection can be determined.

TABLE 13

Single Stranded Conformation Polymorphism (SSCP) Primers

| Sequence ID Number | Variant Name | Primer | Primer Sequence |
|---|---|---|---|
| 39 | IVS2nt19 | Left | 5' t c t c ACTCAAAGAAGAAGTTGGTG 3' |
| 40 | IVS2nt19 | Right | 5' t c c a g a t c c t g t g t t c t t t t c a t t 3' |
| 41 | IVS3nt-22 | Left | 5' t g t c t t a t a a t g t t c t g c c a a t c t g 3' |
| 42 | IVS3nt-22 | Right | 5' AGTTCCGCTCCATAGCTGAGAAT 3' |
| 43 | IVS6nt-7 | Left | 5' g g t g a t g a g c t t t g a g t t t t c t t t 3' |
| 44 | IVS6nt-7 | Right | 5' ATGTCTGATGTACTGTGTGCAGTG 3' |
| 45 | N133N | Left | 5' GTTCCCAAGAACCATTCAAGAG 3' |
| 46 | N133N | Right | 5' t a a c t t c c c t g a t t t a c c t t g a g c 3' |
| 47 | Q232Q | Left | 5' AAGTCCTTGTATAAAACCCATGCT 3' |
| 48 | Q232Q | Right | 5' a t t g a c c c t g a t g t g g a c t t a c TC 3' |
| 49 | V245V | Left | 5' g g t g a t g a g c t t t g a g t t t t c t t t 3' |
| 50 | V245V | Right | 5' ATGTCTGATGTACTGTGTGCAGTG 3' |
| 51 | L321L | Left | 5' GTGCACCTGATGAATACATTGAA 3' |
| 52 | L321L | Right | 5' c t g t a t t t t t c c c a g a t a c c t g c t 3' |
| 53 | L385L | Left | 5' c t t g g g g c c t a c a g TACTGCTTAT 3' |
| 54 | L385L | Right | 5' TCTCCTTGGCATCATTAAAACTCT 3' |
| 55 | Y414Y | Left | 5' c t g t g g t t t t g g t c t t a g GAACTT 3' |
| 56 | Y414Y | Right | 5' CAAAATCTTAAGCTGCTGGGTATT 3' |
| 57 | N426N | Left | 5' c t g t g g t t t t g g t c t t a g GAACTT 3' |
| 58 | N426N | Right | 5' TTAATGGAATCAGCCAAAATCTTA 3' |
| 59 | K274E | Left | 5' AGTCTTCCACTGCACACAGTACAT 3' |
| 60 | K274E | Right | 5' c a a c t g a a c c c a a a c c t c a t t c 3' |
| 61 | A403V | Left | 5' c t g t g t t t t t g g t c t t a g GAACTT 3' |
| 62 | A403V | Right | 5' AAAATCTTAAGCTGCTGGGTATTG 3' | dependent on the base-pair composition of the DNA. The electrophoretic mobility of these single-stranded DNA fragments is dependent on the conformation under non-denaturing conditions. Fragments of PCR-amplified, radioactively labelled DNA are denatured, and then subjected to polyacrylamide gel electrophoresis. A single-base pair variation within the sequence will alter the conformation, and can Significant linkage in these families between the PAH variants and psychiatric diagnosis will be tested by parametric LOD-score analysis and non-parametric linkage analysis (Ghosh, S. et al., "The geneticist's approach to complex disease" *Annu. Rev. Med,* 1996; 47: 333–353).

Some of the variants identified in the DNA study sample show a significant association with Caucasian ethnicity, and the schizophrenic patient with the A403V hyperphenylalanemic mutation is Caucasian. Thus, it would also be of interest, subsequently to conduct a genetic screen for PAH variants on the European-American pedigrees within the NIMH Schizophrenia database (Faraone S V et al., "Genome scan of European-American schizophrenia pedigrees: Results of the NIMH Genetics Initiative and Millennium Consortium, *Am J Med Genet,* 1998, 81:290–295). Moreover, as a similar set of DNA samples are available for the study of bipolar disorder ("Genomic survey of bipolar illness in the NIMH: genetics initiative pedigrees: a preliminary report", *Am J Med Genet,* 1997, 74:227–37), a genetic screen for PAH variants on the NIMH Bipolar Disorder database may be achieved through the SSCP method.

Additional studies include screening all of the PAH variants listed in Example 1 in an additional group of at minimum 75 men with Psychotic, Mood and Personality Disorders, from whom samples have already been collected and are available for DNA analysis. Most of these men participated in the BCAA treatment trials (Background, Studies 4 & 5). The analysis of these data will test the relationship between treatment response to the BCAA and PAH variants in the psychiatric rating scales of the Brief Psychiatric Rating Scale, Hamilton Rating Scale for Depression, Negative Symptom Rating Scale, and the Mini-Mental State Exam (Overall J E, "The Brief Psychiatric Rating Scale" *Psychol. Rep.,* 1962; 10: 799–812; Hamilton M, "A rating scale for depression" *Journal of Neurology, Neurosurgery, and Psychiatry* 1960; 23: 56–62; Folstein M J, "Mini-Mental State. A practical method for grading the cognitive state of patients for the clinician" *J. Psychiat. Res.,* 1975; 12: 189–198).

If the findings of these studies establish PAH gene mutations and polymorphisms as markers of the susceptibility to the development of Psychotic, Mood and Personality Disorders, these PAH variants may be used in screening methods to detect susceptibility to such disorders. In much the same way that screening all newborns for high levels of plasma Phe for the purpose of diagnosing phenylketonuria (PKU) has decreased the economic, social and psychological cost of carrying a PKU PAH mutation in the western world, application of a method for screening the presence of the inventive PAH variants may be used to diagnose susceptibility to schizophrenia.

An alternative method for detection of the mutation K274E will be by the use of an immunological assay. The novel K274E genetic polymorphism, which is significantly associated with the diagnosis of schizophrenia and encodes a lysine to glutamic acid substitution at amino acid 274 in the cofactor binding domain of the PAH protein, results in two possible genetic alleles which can be designated PAH/K and PAH/E. The isoforms of the PAH protein which correlate to the PAH/K or PAH/E alleles may be detected using immunologic assays that employ allele-specific antibodies such as those obtained by monoclonal antibody technique. For example, monoclonal antibodies to the PAH alleles may be produced using hybridoma cell lines as previously described (Cole SP et al., "Human monoclonal antibodies", *Mol Cell Biochem,* 1984, 62:109–120).

Antibodies, whether monoclonal or polyclonal, can be generated using a purified PAH antigen, in particular a PAH protein produced by recombinant DNA means. The antibodies may be produced by any number of species, such as mice, rabbits or humans. Immunoglobulins may be selected from IgG, IgM, IgA, IgD and IgE classes, and may be whole antibodies, fragments or single-chain antibodies, and may also be chimeric antibodies.

Signal generating moieties which may be used to tag an allele-specific antibody or a secondary antibody which binds to an allele-specific antibody include, but are not limited to, those derived from fluorescent dyes, radioisotopes and enzymes.

Immunologic assays which may be used to identify the mutant PAH/E allele in a biological sample from an individual include, but are not limited to, those performed in an ELISA or RIA format, preferably in a manner suitable for clinical diagnostic studies. Other assays include Western blotting and immunoprecipitation.

Example 9

Treatment and Prophylactic Treatment of Susceptibility to Schizophrenia with the Use of the Invention The presence of the K274E mutation in persons with Schizophrenia, and in first and second degree relatives of persons with the disorder, along with (a) the putative changes in the chemical, structural and regulatory properties of the PAH protein caused by the mutation, (b) the significant physiological changes seen with higher plasma Phe levels subsequent to a Phe dose, reduced Phe catabolism to tyrosine, and increased $BH_4$ synthesis in schizophrenics with the mutation, may be used to justify the use of a treatment or prevention strategy that includes the use of the BCAA medical food product already developed by the Inventor.

In the Background to the Invention, a study (Study 4) is presented of the BCAA in TD which showed a statistically and clinically significant decrease in TD symptoms after two weeks of treatment (Richardson M A, Bevans M L, Weber J B, Gonzalez J J, Flynn C J, Read L L, Suckow R F, Maher T J: Branched chain amino acids decrease tardive dyskinesia symptoms. Psychopharmacology, in press; Richardson, M. A. et al., "A dietary intervention decreases tardive dyskinesia symptoms" *Am. Psychiatr. Assoc.,* 149*th Annual Meeting,* New York, N.Y. 1996; 194; Richardson, M. A. et al., "TD symptom decreases with regulation of plasma large neutral amino acids. Schizophrenia Research 1997; 24:272; Richardson, M. A. et al., "TD symptom decreases with regulation of plasma large neutral amino acids" *Abstracts,* 16*th International Congress of Nutrition,* Montreal, Canada 1997; 42). Table 16 demonstrates the decreases in plasma Phe level and the plasma Phe/large neutral amino acid ratios in response to the admininstration of the BCAA, and the resultant plasma increases in plasma BCAA from that study. Similar findings have been reported in a study where administration of BCAA therapy, of a similar composition to that used in the present study, significantly decreased cerebrospinal fluid levels of Phe (Berry H K et al., Reduction of cerebrospinal fluid phenylalanine after oral administration of valine, isoleucine and leucine. Pediatr Res 16: 1982; 751–755; Berry H K et al., Preliminary support for the oral administration of valine, isoleucine, and leucine for phenylketonuria. Dev Med Child Neurol 1985; 27: 33–39; Berry H K et al., Valine, isoleucine, and leucine. A new treatment for phenylketonuria. Amer J of Diseases of Children 1990; 144: 539–543).

It is this effect of BCAA which may be used to mitigate the higher plasma Phe seen with the K274E mutation, and may be a method of treating schizophrenic symptoms or preventing the development of the disorder.

TABLE 14

Mean Plasma Levels of LNAA and LNAA Ratios - Fasting and Post BCAA Administration

| Plasma Amino Acids | Before BCAA Administration (Fasting) | | 2 Hours After BCAA Administration | | % Change | |
|---|---|---|---|---|---|---|
| | Mean | sd | Mean | sd | Mean | sd |
| Measured after one week of BCAA administration: | | | | | | |
| Levels (nmol/ml): | | | | | | |
| BCAA | 472.44 | 77.64 | 1234.56 | 213.75 | +167 | 46 |
| Phenylalanine | 56.33 | 10.85 | 29.44 | 8.65 | −49 | 8 |
| LNAA Ratios: | | | | | | |
| BCAA | 2.80 | 0.44 | 12.95 | 3.49 | +373 | 108 |
| Phenylalanine | 0.12 | 0.01 | 0.02 | 0.01 | −80 | 6 |
| Measured after two weeks of BCAA administration: | | | | | | |
| Levels (mnol/ml): | | | | | | |
| BCAA | 476.56 | 70.08 | 1112.22 | 179.59 | +140 | 37 |
| Phenylalanine | 55.00 | 10.09 | 27.22 | 8.00 | −51 | 8 |
| LNAA Ratios: | | | | | | |
| BCAA | 2.71 | 0.43 | 11.71 | 2.69 | +334 | 78 |
| Phenylalanine | 0.11 | 0.02 | 0.02 | 0.01 | −79 | 5 |

In Study 4, psychiatric symptoms were monitored by use of the Brief Psychiatric Rating Scale (Overall J E, "The Brief Psychiatric Rating Scale" Psychol. Rep., 1962; 10: 799–812). The nine patients who completed two weeks of BCAA treatment were all afflicted with Psychotic Disorders as follows; Schizophrenia (n=6), Schizoaffective Disorder (n=1), Psychotic Disorder, not otherwise specified (n=1), Substance-Induced Psychotic Disorder (n=1). For the group of nine patients in that study, a statistically significant decrease was seen in the Anxiety-Depression factor of that scale (Wilcoxon signed rank test, Z score=2.201; p value=0.0277) and a close to significant decrease was seen in the Thought Disturbance factor of that scale (Wilcoxon signed rank test, Z score=1.887; p value=0.0592). The symptoms included in the Anxiety-Depression factor are the symptoms of somatic concern, anxiety, guilt feelings and depressive mood, and those of the Thought Disturbance factor are the symptoms of conceptual disorganization, grandiosity, hallucinatory behavior, and unusual thought content. These findings support a method of treatment using the BCAA in those with the K274E mutation for either the treatment or prevention of Psychotic Disorders.

The branched chain amino acid formulation to be used (valine:isoleucine:leucine:: 3:3:4) has been used as a treatment modality for TD and was described in Studies 4 and 5 in the Background of the Invention.

The following two categories of persons would be candidates for use of the BCAA treatment regimen:
1. persons diagnosed with the K274E mutation and schizophrenia; and
2. first and second degree relatives of persons with schizophrenia who carry the K274E mutation. Additionally, plasma analyses will be conducted of fasting levels of Phe, tyrosine, neopterin, biopterin and two-hour clearance levels of Phe and tyrosine in this second group.

The method of collecting and using the plasma analysis data for the family members will be conducted as follows:
1. After an overnight fast, fasting blood samples would be drawn, a 100 mg/kg dose of Phe will be administered and two-hour post Phe ingestion bloods would again be drawn for the amino acid and pterin assays.
2. Using the range of data from the schizophrenic patients with the K274E mutation, it would be expected that the family members with the mutation would have a minimum post-dose Phe level of approximately 515 nmol/ml; have a maximum change from fasting to post Phe dose levels of tyrosine of approximately 57%; neopterin levels in the range of 0.0025 nmol/ml to 0.0038 nmol/ml, biopterin levels in the range of 0.0095 nmol/ml to 0.0181 nmol/ml; and a neopterin/biopterin ratio in the range of 0.1644 to 0.3368.

Amino acid analysis can be done in any clinical chemistry laboratory. Biopterin and neopterin levels, however need to be assayed in specialized laboratories. The amino acid methods to be used are the same as those used in the DNA study and have been described in Example 4. The pterin assay methods are as follows.

Assay of neopterins and biopterins will be performed by using high performance liquid chromatography with fluorescent detection (Hyland-K et.al., Oral phenylalanine loading in dopa-responsive dystonia: A possible diagnostic test, *Neurology* 1997 48 1290–1297.) and by high performance liquid chromatography using an ion-paired reverse phase system and fluorometric detection (Fukushima T et al., "Analysis of reduced forms of biopterin in biological tissues and fluids", *Analytical Biochemistry*, 102:176–188, 1980; Lunte C E and Kissinger P T, "Determination of pterins in biological samples by liquid chromatography/electrochemistry with a dual-electrode detector", *Analytical Chemistry*, 55:1458–1462, 1983). The measurement for total biopterins includes the tetrahydrobiopterin ($BH_4$), dihydrobiopterin and biopterin forms, and about 90% of the total is in the form of $BH_4$. The measurement for total neopterins includes the dihydroneopterin and neopterin forms (Levine, R. A. "Tetrahydrobiopterin and biogenic amine metabolism in neuropsychiatry, immunology, and aging" *Annals of the New York Academy of Sciences* 1988; 521: 129–139., Kay, A. D. et al., "Cerebrospinal fluid biopterin is decreased in Alzheimer's disease" *Arch. Neurol.* 1986; 43: 996–999.).

There is a long felt need in the field for targeted strategies for the treatment of subtypes of schizophrenics. Further, there are no approaches that are applicable to the prophylactic methods of treatment for these disorders. The present invention establishes a defined treatment and prophylactic treatment rationale for a subtype of patients within an ethnic group, and advances the field accordingly. Further, the possible definition of the candidates for treatment that combines a genetic mutation marker with a defined physiological mechanism which is further marked by a specific plasma response to a challenge has not been matched in the field. Additionally, the fact that the treatment approach involves the use of a medical food that has proven to be safe and effective for a central nervous system disorder, and is within the same framework that has been successful in preventing the development of the symptoms of PKU, a disorder caused by PAH deficiency adds feasibility to practice of the invention.

Example 10

Gene and Protein Therapies for Affected Individuals

The identification of mutations and polymorphisms in the phenylalanine hydroxylase gene (SEQ ID Nos. 27–38) in individuals with psychiatric disorders, suggests that therapies which provide affected individuals with the normal phenylalanine hydroxylase gene or protein, can be developed.

It is contemplated that cells expressing a normal phenylalanine hydroxylase gene will be introduced into affected individuals, as therapeutic agents. Skilled artisans will recognize the appropriate bodily regions for the placement of cells useful to treat phenylalanine hydroxylase deficiencies or abnormalities, and will be able to ascertain cell types useful for such therapies. Many methods of cell delivery are known in the art, including implantation of membrane encapsulated cells (Aebischer et al., *Experimental Neurology,* 1991, 111: 269–275).

In addition, it is contemplated that a normal PAH gene will be introduced into affected individuals using gene therapy strategies. Vectors, particularly viral vectors, containing a normal gene may be useful in the gene therapy.

Genes and vectors may be delivered by many methods known in the art including, but not limited to, liposome delivery and viral transduction. The expression of the normal gene thus delivered can be regulated in vivo by methods including those described by Burcin M M et al. ("Adenovirus-mediated regulable target gene expression in vivo",*Proc Nat Acad Sci. USA,* 1999, 96:355–360) and Ye X et al. ("Regulated delivery of therapeutic proteins after in vivo somatic cell gene transfer",*Science,* 1999, 283:88–94).

Furthermore, normal phenylalanine hydroxylase protein may be useful in treating affected individuals. Protein can be introduced to desired organs or tissues by a variety of methods which include, but are not limited to, liposome delivery, bolus delivery, or intravenous drip.

---

What is claimed:

1. A method for treating schizophrenia in a human patient, comprising administering to the human patient an effective amount of a combination of valine, leucine, and isoleucine in the absence of aromatic amino acids.

2. The method of claim 1, wherein the effective amount of a combination of valine, leucine, and isoleucine is in a ratio of 3:3:4.

3. A method for treating bipolar disorder in a human patient comprising administering to the human patient an effective amount of a combination of valine, leucine, and isoleucine in the absence of aromatic amino acids.

4. The method of claim 3, wherein the effective amount of a combination of valine, leucine, and isoleucine is in a ratio of 3:3:4.

* * * * *